United States Patent
Zanghellini et al.

(10) Patent No.: US 10,025,900 B2
(45) Date of Patent: Jul. 17, 2018

(54) AUTOMATED METHOD OF COMPUTATIONAL ENZYME IDENTIFICATION AND DESIGN

(71) Applicants: Alexandre Zanghellini, Seattle, WA (US); Yih-En Andrew Ban, Seattle, WA (US); Eric Anthony Althoff, Seattle, WA (US); Daniela Grabs, Seattle, WA (US); Mihai Luchian Azoitei, Chapel Hill, NC (US)

(72) Inventors: Alexandre Zanghellini, Seattle, WA (US); Yih-En Andrew Ban, Seattle, WA (US); Eric Anthony Althoff, Seattle, WA (US); Daniela Grabs, Seattle, WA (US); Mihai Luchian Azoitei, Chapel Hill, NC (US)

(73) Assignee: ARZEDA CORP., Seattle, WA (US)

( * ) Notice: Subject to any disclaimer, the term of this patent is extended or adjusted under 35 U.S.C. 154(b) by 0 days.

(21) Appl. No.: 14/776,532

(22) PCT Filed: Mar. 14, 2014

(86) PCT No.: PCT/US2014/029589
§ 371 (c)(1),
(2) Date: Sep. 14, 2015

(87) PCT Pub. No.: WO2014/144963
PCT Pub. Date: Sep. 18, 2014

(65) Prior Publication Data
US 2016/0063177 A1    Mar. 3, 2016

Related U.S. Application Data

(60) Provisional application No. 61/793,598, filed on Mar. 15, 2013.

(51) Int. Cl.
| | | |
|---|---|---|
| C12N 9/04 | (2006.01) | |
| C12N 9/18 | (2006.01) | |
| C12N 9/86 | (2006.01) | |
| G06G 7/58 | (2006.01) | |
| G06F 19/16 | (2011.01) | |
| G06F 19/18 | (2011.01) | |
| G06F 17/50 | (2006.01) | |

(52) U.S. Cl.
CPC ............. *G06F 19/16* (2013.01); *G06F 17/50* (2013.01); *G06F 19/18* (2013.01)

(58) Field of Classification Search
None
See application file for complete search history.

(56) References Cited

U.S. PATENT DOCUMENTS

| | | | |
|---|---|---|---|
| 6,792,356 B2 | 9/2004 | Mayo et al. | |
| 7,574,306 B1 | 8/2009 | Baker et al. | |
| 8,340,951 B2 | 12/2012 | Baker et al. | |
| 2002/0183937 A1* | 12/2002 | Mayo | G06F 19/16 702/19 |
| 2009/0319193 A1* | 12/2009 | Yang | G06F 19/16 702/19 |

FOREIGN PATENT DOCUMENTS

WO    WO 2014/144963 A1    9/2014

OTHER PUBLICATIONS

Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Kisselev L., Polypeptide release factors in prokaryotes and eukaryotes: same function, different structure. Structure, 2002, vol. 10: 8-9.*
International Preliminary Report on Patentability for International Application No. PCT/US2014/029589, dated Sep. 15, 2015, 7 pages.
International Search Report and Written Opinion for International Application No. PCT/US2014/029589, dated Aug. 19, 2014, 9 pages.
Zanghellini, A., et al., "New algorithms and an in silico benchmark for computational enzyme design." Protein Science (2006); 15(12): 2785-2794.

* cited by examiner

*Primary Examiner* — Iqbal H Chowdhury
(74) *Attorney, Agent, or Firm* — Cooley LLP

(57) ABSTRACT

The invention provides computational methods for engineering, selecting, and/or identifying proteins with a desired activity. Further provided are automated computational design and screening methods to engineer proteins with desired functional activities including, but not limited to ligand binding, catalytic activity, substrate specificity, regioselectivity and/or stereoselectivity.

22 Claims, 28 Drawing Sheets

FIG. 5

```
Mar 14, 13 6:51                    TS.cst                        Page 1/1
# ###################################################

# BETA-GLYCOSIDASE ACTIVE SITE PARAMETERS
# SUBSTRATE: para-nitrophenyl glucose

# ....................................................

# Copyright (c) 2010-2013 Arzeda Corporation

################################################### constraint file for R group flexibility

CST::BEGIN

TEMPLATE::   ATOM_MAP: 1 atom_name: O2 C7 C10
  TEMPLATE::   ATOM_MAP: 1 residue3: LG1

TEMPLATE::   ATOM_MAP: 2 atom_type: OOC
  TEMPLATE::   ATOM_MAP: 2 residue1: E

CONSTRAINT:: distanceAB:   3.0    0.5    50.0   1
  CONSTRAINT::    angle_A:  109.5   5.0    50.0  360.
  CONSTRAINT::    angle_B:  120.0   5.0    50.0  360.
  CONSTRAINT::   torsion_A:   0.0   0.0     0.0  360.
  CONSTRAINT::  torsion_AB:   0.0   0.0     0.0  360.
  CONSTRAINT::   torsion_B: 180.0  10.0    50.0  180.

CST::END

CST::BEGIN

TEMPLATE::   ATOM_MAP: 1 atom_name: C1 O2 C7
  TEMPLATE::   ATOM_MAP: 1 residue3: LG1

TEMPLATE::   ATOM_MAP: 2 atom_type: OOC
  TEMPLATE::   ATOM_MAP: 2 residue1: E

CONSTRAINT:: distanceAB:   2.0    0.5    50.0   1
  CONSTRAINT::    angle_A:  180.0  10.0    50.0  360.
  CONSTRAINT::    angle_B:  120.0  10.0    50.0  360.
  CONSTRAINT::   torsion_A:   0.0   0.0     0.0  360.
  CONSTRAINT::  torsion_AB:   0.0   0.0     0.0  360.
  CONSTRAINT::   torsion_B: 180.0  10.0    50.0  360.

CST::END

CST::BEGIN

TEMPLATE::   ATOM_MAP: 1 atom_type: OH
  TEMPLATE::   ATOM_MAP: 1 residue1: Y

TEMPLATE::   ATOM_MAP: 2 atom_type: OOC
  TEMPLATE::   ATOM_MAP: 2 residue1: E

CONSTRAINT:: distanceAB:   2.7    0.3    50.0   0
  CONSTRAINT::    angle_A:   0.0   0.0     0.0  360.
  CONSTRAINT::    angle_B:   0.0   0.0     0.0  360.
  CONSTRAINT::   torsion_A:   0.0   0.0     0.0  360.
  CONSTRAINT::  torsion_AB:   0.0   0.0     0.0  360.
  CONSTRAINT::   torsion_B:   0.0   0.0     0.0  360.

CST::END
```

A
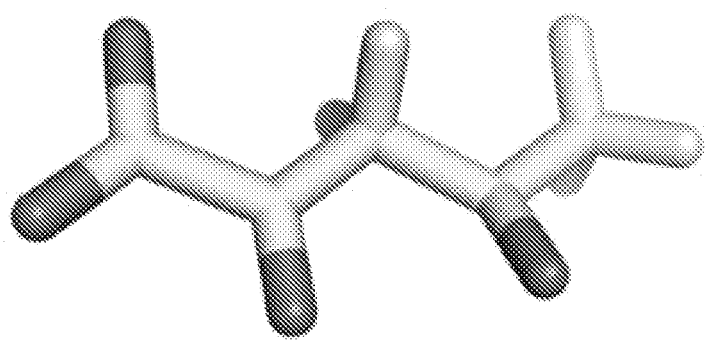
B
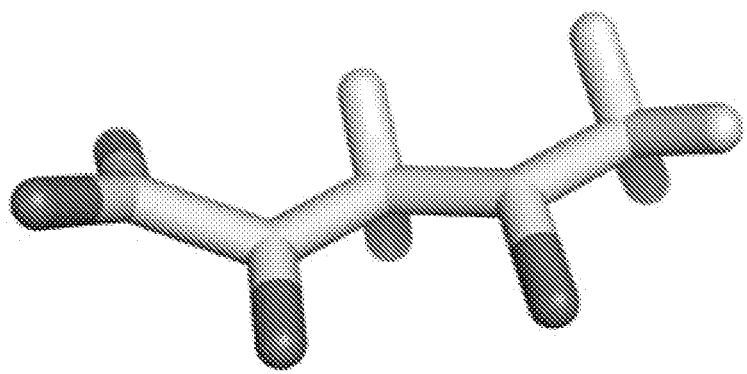
FIG. 21

| EC Number | Enzyme Name | Cofactor | Representative PDB code |
|---|---|---|---|
| | Alcohol dehydrogenase (NAD+) | NADH | 3ox4 |
| | Alcohol dehydrogenase (NAD+) | NADH | 2hcy |
| 1.1.1.1 | Alcohol dehydrogenase (NAD+) | NADH | 1r37 |
| | Alcohol dehydrogenase (NADP+) | NAD(P)H | 1frb |
| | Alcohol dehydrogenase (NADP+) | NAD(P)H | 3cv7 |
| 1.1.1.2 | Alcohol dehydrogenase (NADP+) | NAD(P)H | 1ix4 |
| 1.1.1.3 | Homoserine dehydrogenase | NAD(P)H | 1ebu |
| 1.1.1.6 | Glycerol dehydrogenase | NADH | 1jq5 |
| 1.1.1.8 | Glycerol-3-phosphate dehydrogenase | NADH | 1n1e |
| 1.1.1.9 | D-xylose reductase | NAD(P)H | 1zem |
| 1.1.1.10 | L-xylulose reductase | NADPH | 1wnt |
| 1.1.1.14 | L-iditol 2-dehydrogenase | NADH | 1pl6 |
| 1.1.1.16 | Galactitol 2-dehydrogenase | NADH | 3lqf |
| 1.1.1.18 | Inositol 2-dehydrogenase | NADH | 3nt2 |
| 1.1.1.21 | Aldehyde reductase | NAD(P)H | 1k2c |
| 1.1.1.22 | UDP-glucose 6-dehydrogenase | NADH | 2q3e |
| 1.1.1.24 | Quinate dehydrogenase | NADH | 3jyo |
| 1.1.1.25 | Shikimate dehydrogenase | NADPH | 2ev9 |
| 1.1.1.26 | Glyoxylate reductase | NAD(P)H | 2dbq |
| 1.1.1.27 | L-lactate dehydrogenase | NAD(P)H | 1i8h |
| 1.1.1.28 | D-lactate dehydrogenase | NADH | 3kb6 |
| 1.1.1.29 | Glycerate dehydrogenase | NAD(P)H | 1gdh |
| 1.1.1.30 | 3-hydroxybutyrate dehydrogenase | NADH | 2zti |
| 1.1.1.31 | 3-hydroxyisovalerate dehydrogenase | NAD(P)H | 2f9p |
| | 3-hydroxyacyl-CoA dehydrogenase | NAD(P)H | 1e3w |
| 1.1.1.35 | 3-hydroxyacyl-CoA dehydrogenase | NAD(P)H | 3hdh |
| 1.1.1.36 | Acetoacetyl-CoA reductase | NAD(P)H | 3gk3 |
| 1.1.1.37 | Malate dehydrogenase | NAD(P)H | 1emd |
| 1.1.1.39 | Malate dehydrogenase | NAD(P)H | 1do8 |
| 1.1.1.40 | Malate dehydrogenase (oxaloacetate decarboxylating) | NADPH | 1gq2 |
| 1.1.1.42 | Isocitrate dehydrogenase | NADPH | 2qfx |
| 1.1.1.44 | Phosphogluconate dehydrogenase (decarboxylating) | NAD(P)H | 2iyp |
| 1.1.1.45 | L-gulonate 3-dehydrogenase | NADH | 3odo |
| 1.1.1.47 | glucose 1-dehydrogenase | NAD(P)H | 2cdb |
| 1.1.1.49 | glucose-6-phosphate dehydrogenase | NAD(P)H | 2bh9 |
| 1.1.1.50 | 3alpha-hydroxysteroid dehydrogenase | NAD(P)H | 2dkn |
| 1.1.1.51 | 3beta/17beta hydroxysteroid dehydrogenase | NAD(P)H | 1hxh |
| 1.1.1.52 | 3alpha-hydroxycholanate dehydrogenase | NADH | 3lhj |
| 1.1.1.53 | 3alpha/20beta hydroxysteroid dehydrogenase | NAD(P)H | 1nfq |
| 1.1.1.60 | 2-hydroxy-3-oxopropionate reductase | NAD(P)H | 1yb4 |
| 1.1.1.62 | estradiol 17beta dehydrogenase | NAD(P)H | 1zq5 |
| 1.1.1.67 | mannitol dehydrogenase | NADH | 1m2w |
| 1.1.1.69 | gluconate 5-dehydrogenase | NAD(P)H | 3cd3 |
| 1.1.1.77 | lactaldehyde reductase | NAD(P)H | 1rrm |
| 1.1.1.79 | glyoxylate reductase (NADP) | NADPH | 3kb6 |
| 1.1.1.82 | malate dehydrogenase (NADP) | NADPH | 7mdh |
| 1.1.1.83 | Malate dehydrogenase (decarboxylating) | NADH | 3fmx |
| 1.1.1.85 | isopropylmalate dehydrogenase | NADH | 2v41 |
| 1.1.1.90 | aryl-alcohol dehydrogenase | NADH | 1f8f |
| 1.1.1.93 | tartrate dehydrogenase | NADH | 3fix |
| 1.1.1.94 | glycerol-3-phosphate dehydrogenase | NADPH | 2zb2 |

*FIG. 27*

| EC Number | Enzyme Name | Cofactor | Representative PDB code |
|---|---|---|---|
|  | phosphoglycerate dehydrogenase | NADH | 1yba |
| 1.1.1.95 | phosphoglycerate dehydrogenase | NADH | 2g76 |
| 1.1.1.100 | 3-oxoacyl-[acyl-carrier-protein] reductase | NADPH | 1q7b |
| 1.1.1.103 | L-threonine 3-dehydrogenase | NADH | 3o4v |
| 1.1.1.107 | pyridoxal 4-dehydrogenase | NAD(P)H | 3nig |
| 1.1.1.112 | indanol dehydrogenase | NAD(P)H | 3nty |
| 1.1.1.117 | D-arabinose 1-dehydrogenase (NADP) | NADPH | 2h6e |
| 1.1.1.118 | glucose 1-dehydrogenase | NAD(P)H | 2dte |
| 1.1.1.125 | 2-deoxy-D-gluconate 3-dehydrogenase | NADH | 2ekp |
| 1.1.1.126 | 2-dehydro-3-deoxy-D-gluconate 5-dehydrogenase | NADPH | 3afn |
| 1.1.1.132 | GDP-mannose 6-dehydrogenase | NADH | 1muu |
| 1.1.1.133 | dTDP-4-dehydrorhamnose reductase | NAD(P)H | 1kc3 |
| 1.1.1.138 | mannitol 2-dehydrogenase (NADP+) | NADPH | 1h5q |
| 1.1.1.141 | 15-hydroxyprostaglandin dehydrogenase (NAD+) | NADH | 2gdz |
| 1.1.1.146 | 11beta-hydroxysteroid dehydrogenase | NAD(P)H | 3g49 |
| 1.1.1.149 | 20alpha-hydroxysteroid dehydrogenase | NAD(P)H | 1mrq |
| 1.1.1.153 | sepiapterin reductase | NADH | 1oaa |
| 1.1.1.154 | ureidoglycolate dehydrogenase / delta1-piperideine-2-carboxylat | NAD(P)H | 2cwf |
| 1.1.1.159 | 7alpha-hydroxysteroid dehydrogenase | NADH | 1fmc |
| 1.1.1.169 | 2-dehydropantoate 2-reductase | NADPH | 2ofp |
| 1.1.1.178 | 3-hydroxy-2-methylbutyryl-CoA dehydrogenase | NADH | 2o23 |
|  | carbonyl reductase | NADPH | 3blm |
| 1.1.1.184 | carbonyl reductase | NADPH | 2cyd |
| 1.1.1.188 | prostaglandin-F synthase | NADH | 1vbj |
| 1.1.1.189 | prostaglandin-E2 9-reductase | NADPH | 1q13 |
| 1.1.1.193 | 5-amino-6-(5-phosphoribosylamino)uracil reductase | NADPH | 2azn |
| 1.1.1.195 | cinnamyl-alcohol dehydrogenase | NADPH | 2cf6 |
| 1.1.1.197 | 15-hydroxyprostaglandin dehydrogenase | NADPH | 2zat |
| 1.1.1.202 | 1,3-propanediol dehydrogenase | NADH | 3bfj |
| 1.1.1.209 | 3(or 17)alpha-hydroxysteroid dehydrogenase | NADPH | 2ipf |
| 1.1.1.213 | 3alpha-hydroxysteroid dehydrogenase | NAD(P)H | 1hwi |
| 1.1.1.218 | morphine 6-dehydrogenase | NAD(P)H | 2wzm |
| 1.1.1.219 | dihydrokaempferol 4-reductase | NADPH | 2c29 |
| 1.1.1.236 | tropinone reductase II | NADPH | 1ixl |
| 1.1.1.237 | hydroxyphenylpyruvate reductase | NADH | 3haz |
| 1.1.1.248 | salutaridine reductase | NADPH | 3o26 |
| 1.1.1.252 | tetrahydroxynaphthalene reductase | NADPH | 1doh |
| 1.1.1.253 | pteridine reductase | NADPH | 1e92 |
| 1.1.1.263 | 1,5-anhydro-D-fructose reductase | NAD(P)H | 2glx |
| 1.1.1.267 | 1-deoxy-D-xylulose-5-phosphate reductoisomerase | NAD(P)H | 1q1q |
| 1.1.1.268 | 2-R-hydroxypropyl-CoM dehydrogenase | NADH | 2cfc |
| 1.1.1.272 | R-2-hydroxyacid dehydrogenase | NAD(P)H | 2x8i |
| 1.1.1.274 | 2,5-didehydrogluconate reductase | NADPH | 1vp5 |
| 1.1.1.275 | trans-carveol dehydrogenase | NADH | 3pox |
| 1.1.1.276 | serine 3-dehydrogenase | NADPH | 3q1c |
| 1.1.1.284 | S-(hydroxymethyl) glutathione dehydrogenase | NAD(P)H | 3qj5 |
| 1.1.1.289 | sorbose reductase | NADPH | 3ai3 |
| 1.1.1.290 | 4-phosphoerythronate dehydrogenase | NADH | 2o4c |
| 1.1.1.311 | (S)-1-phenylethanol dehydrogenase | NADH | 2ewm |

*FIG. 27 (Continued)*

AUTOMATED METHOD OF COMPUTATIONAL ENZYME IDENTIFICATION AND DESIGN

CROSS REFERENCE TO RELATED APPLICATIONS

This application claims the benefit under 35 U.S.C. § 119(e) of U.S. Provisional Application No. 61/793,598, filed Mar. 15, 2013, which is incorporated by reference in its entirety.

BACKGROUND

Technical Field

The invention relates generally to computational methods for obtaining proteins with a desired activity. More particularly, the invention relates to using automated computational methods to predict, produce, identify, screen for, and optionally design proteins with desired functional activities including, but not limited to ligand binding, catalytic activity, substrate specificity, regioselectivity and/or stereoselectivity.

BRIEF SUMMARY

In various embodiments, the present invention contemplates, in part, automated, high-performance computational methods for automatically predicting or screening, in a timely manner, amino-acid sequence databases to identify protein sequences most likely to have a desired functional activity. As used herein, the term "functional activity" refers to any one or more of the following: ligand binding, catalytic activity, substrate specificity and/or stereoselectivity, or any suitable combination thereof "Ligands" refer to one or more small-molecules, ribonucleotides, peptides, polypeptides, polymers, or any suitable combination thereof. As used herein, the term "substrate" refers to a molecule that is acted upon by an enzyme. The protein amino-acid sequences selected from the databases may be further constructed as DNA sequences, cloned into a suitable plasmid, and expressed in a suitable organism for experimental validation. In another aspect, methods contemplated herein are used to select a set of protein sequences that are subsequently altered and engineered to enable a protein comprising a desired functional activity. Said alteration or engineering of the sequence may use the technique of computational protein design (as disclosed in patent U.S. Pat. No. 7,574,306 and U.S. Pat. No. 8,340,951, which are hereby incorporated by reference in their entirety) directed evolution techniques, rational mutagenesis, or any suitable combination thereof.

In one embodiment, a method for making, screening for, or identifying a protein having a desired function comprises four steps. In a first aspect, a template structure is obtained from an experimentally derived three-dimensional protein structure, typically obtained through experimental methods including, but not limited to, x-ray crystallography, nuclear magnetic resonance (NMR), scattering, or diffraction techniques. The template structure contains coordinate information for all or a subset of the protein atoms where the protein is known or predicted to harbor the function of interest, or a similar function (for instance, binding of a structurally close substrate, or catalyzing a chemically related reaction). Optionally, the information describing the template structure contains a geometric description of the functional site of the protein, comprising one or more of (1) structural models of ligands, and in the case of enzyme structural models of one or multiple transition state(s) along the reaction catalyzed, and/or structural models of reaction product(s), (2) a description of the allowed identities and rotameric states for each functional residue composing the functional site, and (3) the geometric placement of said functional residues with respect to the ligand(s), transition state(s), product(s) and transition models (usually, but not necessarily, encoded as mathematically expressed constraints).

In a second aspect, a structural homology search is carried out. The protein backbone of the template structure is compared to a database of protein structures through a structural homology search algorithm, and all proteins scoring lower than a specified threshold in terms of a suitable structural similarity metric are selected (i.e., the closest homologs). For each such selected homologous structure, the identity and geometric placement of the residues aligned in the homolog to the functional residues of the template structure are checked against the description provided. In particular embodiments, structures that pass the check (hit structures) are considered for the third step, while structures that do not meet the threshold for inclusion are discarded.

In a third aspect, computational docking of the ligand(s), substrate(s), transition state(s) and/or product(s), is carried out in the set of homolog structures selected at the end of the second step in the context of the wild-type sequences corresponding to these homolog structures. The computational docking may include one or more iterations between optimization of the rigid-body positioning of the ligand/substrate/transition state(s)/product(s) with or without simultaneous protein side-chain repacking, discrete and/or continuous optimization of the protein side-chain and main-chain atoms, as well as discrete and/or continuous optimization of the ligand/substrate/transition state(s)/product(s) internal degrees of freedom. Alternatively, computational redesign of the wild-type amino-acid sequence is carried out, preferably through one or more iterations between computational docking and computational redesign, to obtain new sequences predicted to have the desired function.

In a fourth aspect, the protein sequences obtained after the third step are reverse-translated to DNA sequences (preferably codon-optimized to enhance protein expression in the targeted expression organism, including, but not limited to, *Escherichia coli*), and the resulting DNA sequences constructed and cloned into a suitable expression vector. The DNA sequences are then translated and the resulting protein expressed, purified and experimentally assayed to validate the predicted functional activity.

In various embodiments, the present invention contemplates, in part, a method for computational design of, selection of, identification of, or screening for a protein having a desired function activity comprising four steps and relying on a sequence database and homology models in addition to a structural database. A first aspect may be exactly the same as that described supra, e.g, a structural template is obtained from an experimentally derived three-dimensional protein structure, typically obtained through experimental methods including, but not limited to, x-ray crystallography, nuclear magnetic resonance (NMR), scattering, or diffraction techniques, or it may include only an amino-acid template sequence in lieu of the structural template. This is the case, for instance, when a given protein sequence is known to have a function of interest, and the positions and identities of the functional residues and groups in the sequence are known, but no experimentally derived structural information is available.

In a second aspect, a sequence homology search is carried out. The protein sequence of the template, either obtained from said template structure or directly taken from said template sequence, is compared to a database of protein sequences with sequence homology search algorithm such as BLASTP/PSI-BLAST/DELTA-BLAST or HMMER/JackHMMER. In one embodiment, proteins sequences scoring lower than a specified threshold in terms of a suitable sequence similarity metric are selected. In another aspect, the template sequence may be reverse translated to DNA and compared to a database of DNA sequences with sequence homology search algorithms, such as BLAST or HMMER. For each such selected homologous sequences, the position and identity of the residues in the homologous sequence are aligned to functional residues in the template sequence and are checked against the description provided. In one embodiment, sequences that pass the check (hit sequences) are considered for the third aspect, while others are discarded.

In a third aspect, structural databases are searched to find at least one experimentally derived protein structure for each said hit sequence. If this is the case, computational docking of the ligand(s) and/or substrate(s) and/or transition state(s) and/or products, and/or redesign of the wild-type hit sequence is performed as described elsewhere, supra. If no structure exists for a hit sequence, structural models are generated using a homology modeling algorithm such as ROSETTA or MODELLER, optionally using the functional constraints defining the active site geometry as described supra, and elsewhere herein to guide the modeling process. One or several structures may be used as template for modeling. One or several homology models (with the wild-type amino-acid sequence from the original hit sequence) are used for computational docking of the ligand(s) and/or substrate(s) and/or transition state(s) and/or products, and/or redesign of the wild-type sequence as described supra.

In a fourth aspect identical to that described supra, the protein sequences obtained are experimentally assayed for activity.

In a preferred embodiment, a method contemplated herein is used several times through an iterative process. In applying the methods contemplated herein, as described supra and elsewhere herein, the results are structural models and corresponding sequences of proteins predicted, or experimentally verified as having the desired functional activity. These models can be used to generate new sets of template structures, each of which being used in further iterations of the methods contemplated supra and elsewhere herein. One or more, e.g., 1, 2, 3, 4, 5, 6, 7, 8, 9, 10 or more, iterations can be performed to generate a diverse library of proteins with predicted or experimentally confirmed functional activity.

In another preferred embodiment, some or all of the protein sequences of the hit structures obtained from structural homology modeling are used for a sequence homology search as described above: the sequences from the hit structures are used to query one or multiple database(s) to obtain homologous sequences. During homology model building, one or more of the hit structures may be used as structural templates.

Any one or more of the aspects of the methods contemplated supra and elsewhere herein may be implemented as independent software components that need to be run sequentially to practice the invention. In one preferred embodiment, however, part or preferably all said aspects of a method contemplated supra or elsewhere herein are integrated into a single automated tool that requires very little human intervention. For example and typically, the structural and sequence alignment steps, the generation of ligand(s), substrate(s), product(s) and/or transition state(s) structural models, the generation of starting models of unknown protein structures (homology modeling), and computational docking and redesign are combined into one single executable computer file.

BRIEF DESCRIPTION OF THE SEVERAL VIEWS OF THE DRAWINGS

FIG. 5 gives an example of the file describing the allowed identities of catalytic residues for the active site template described in FIG. 3, as well as the description of the geometric constraints that specify the placement of each catalytic residue with respect to the metal, transition state(s), product(s) and transition models (usually, but not necessarily, encoded as mathematically expressed constraints).

FIG. 9 is a copy of the parameterization file (cstfile) used to model the active site of FIG. 8 and to perform constrained-docking of the transition state in the beta-glucosidase structures selected. The three different blocks of statements delimited by the CST::BEGIN and CST::END statements correspond to each of the catalytic residues 1, 2 and 3 in FIG. 8.

Figure 14:
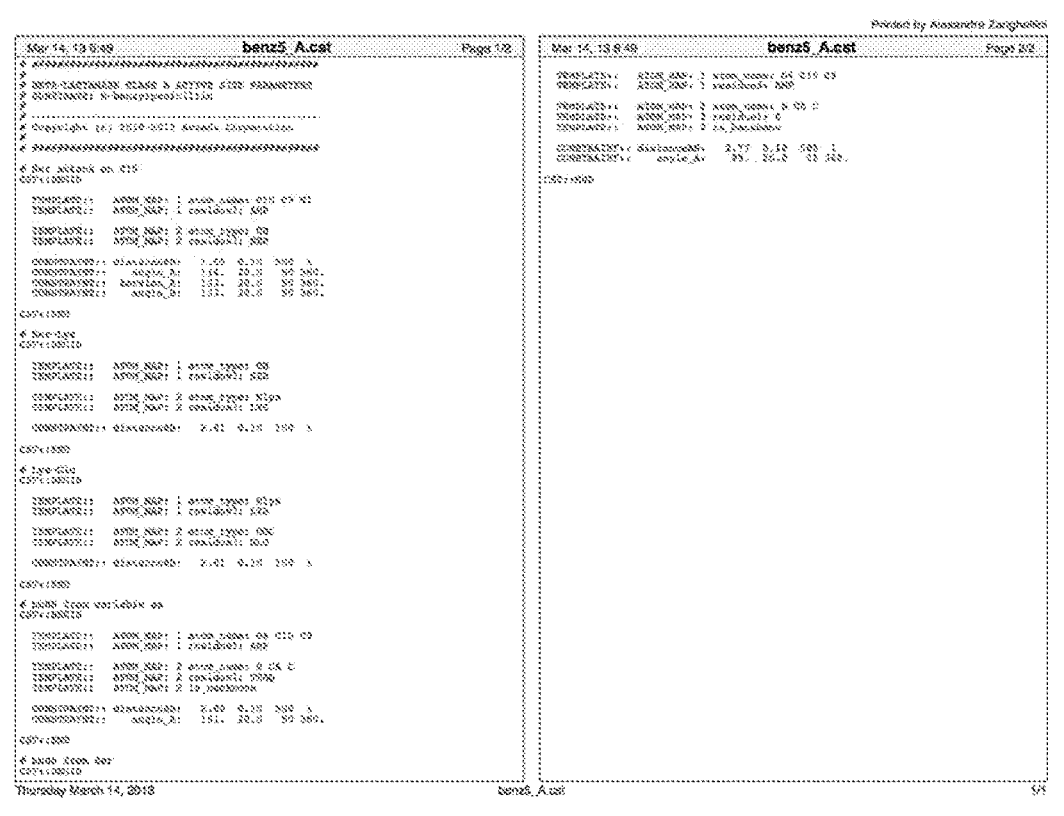

FIG. 14 is a copy of the parameterization file (cstfile) used to model the active site of FIG. 13 and to perform constrained-docking of the (R) stereoisomer of the transition state for the hydrolysis of benzyl-penicillin, in the class A beta-lactamase structures selected. The five different blocks of statements delimited by the CST::BEGIN and CST::END statements correspond to each of the catalytic residues 1, 2, 3 and 4 in FIG. 13. Note that because the catalytic residue 1 (Serine) is involved in two different ways in the active site (as the nucleophile and as provided one key backbone hydrogen bond to form the oxyanion hole), it is attached to two blocks instead of one.

Figure 15:
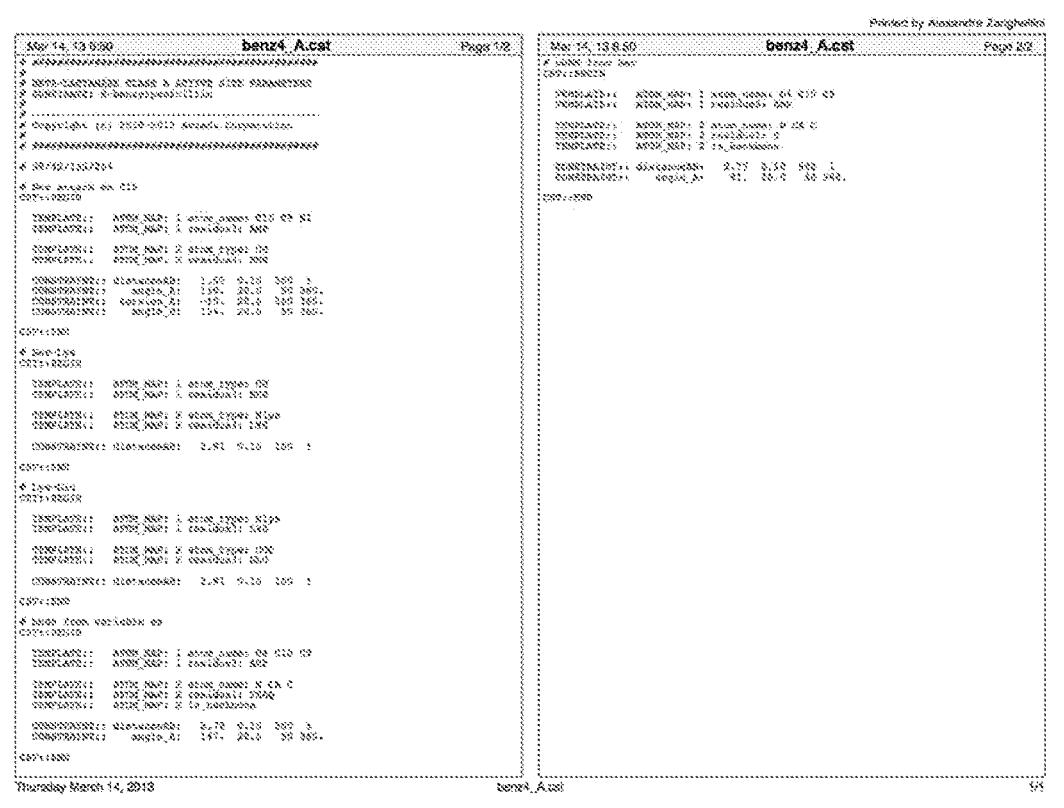

FIG. 15 is a copy of the parameterization file (cstfile) used to model the active site of FIG. 13 and to perform constrained-docking of the (S) stereoisomer of the transition state for the hydrolysis of benzyl-penicillin, in the class A beta-lactamase structures selected. The five different blocks of statements delimited by the CST::BEGIN and CST::END statements correspond to each of the catalytic residues 1, 2, 3 and 4 in FIG. 13. Note that because the catalytic residue 1 (Serine) is involved in two different ways in the active site (as the nucleophile and as provided one key backbone hydrogen bond to form the oxyanion hole), it is attached to two blocks instead of one.

Figure 16:
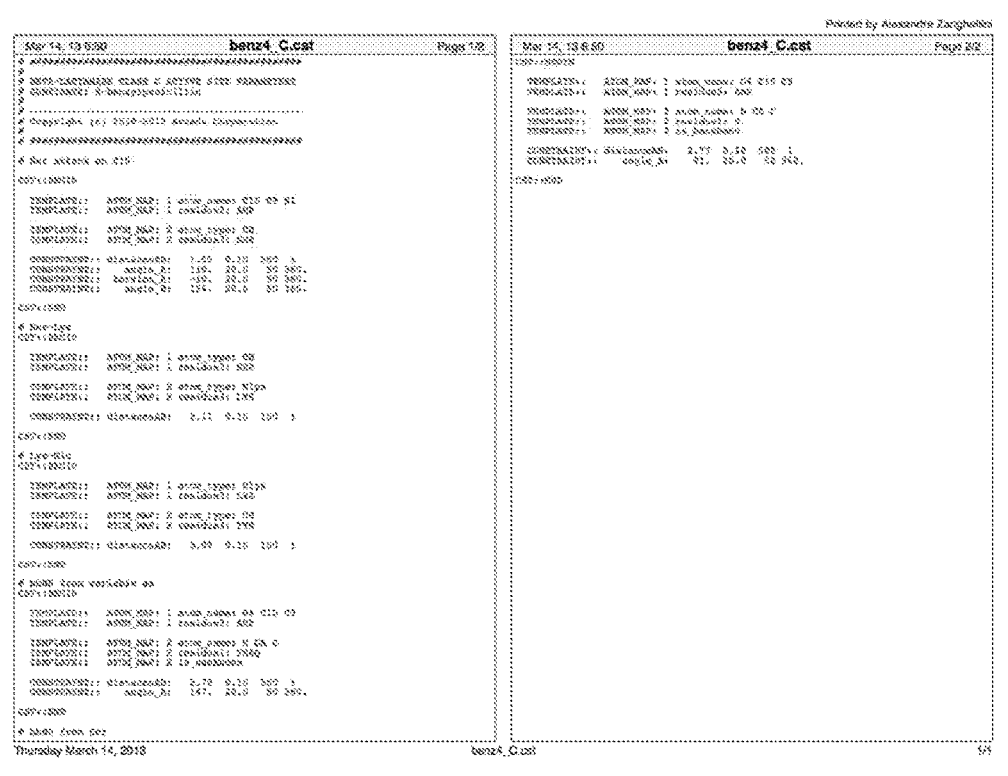

FIG. 16 is a copy of the parameterization file (cstfile) used to model the active site of FIG. 13 and to perform constrained-docking of the (R) stereoisomer of the transition state for the hydrolysis of benzyl-penicillin, in the class C beta-lactamase structures selected. The five different blocks of statements delimited by the CST::BEGIN and CST::END statements correspond to each of the catalytic residues 1, 2, 3 and 4 in FIG. 13. Note that because the catalytic residue 1 (Serine) is involved in two different ways in the active site (as the nucleophile and as provided one key backbone hydrogen bond to form the oxyanion hole), it is attached to two block instead of one.

Figure 17:
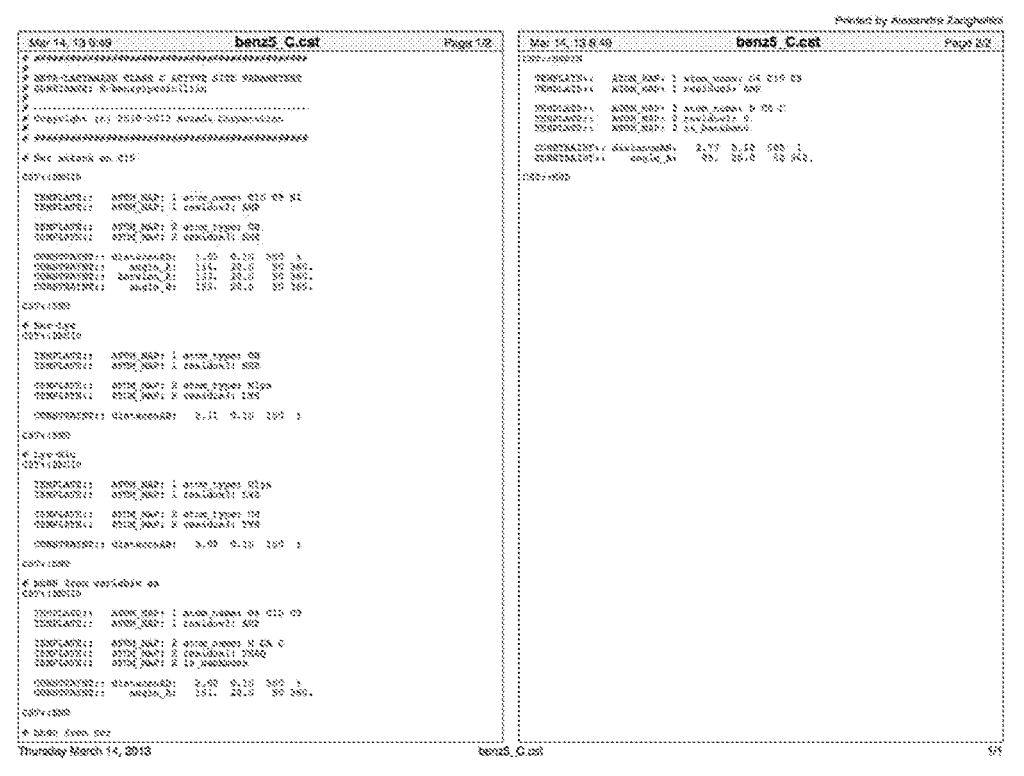

FIG. 17 is a copy of the parameterization file (cstfile) used to model the active site of FIG. 13 and to perform constrained-docking of the (S) stereoisomer of the transition state for the hydrolysis of benzyl-penicillin, in the class C beta-lactamase structures selected. The five different blocks of statements delimited by the CST::BEGIN and CST::END statements correspond to each of the catalytic residues 1, 2, 3 and 4 in FIG. 13. Note that because the catalytic residue 1 (Serine) is involved in two different ways in the active site (as the nucleophile and as provided one key backbone hydrogen bond to form the oxyanion hole), it is attached to two blocks instead of one.

FIG. 21 is a graphical rendering of the consensus models used in Example 3. This consensus model is obtained through geometric interpolation between the substrate 4-hydroxy-2-oxo-pentanoic acid and product 2,4-dioxo-pentanoic acid. The 4(R)-hydroxy-2-oxo-pentanoic acid is in panel A, the 4(S)-hydroxy-2-oxo-pentanoic acid is in panel B.

FIG. 27 is the listing of all the 98 entries of the dehydrogenase/reductase database constructed as described elsewhere herein and used in Example 3. The left column corresponds to the EC number assigned to the enzyme in the Enzyme Classification. The second column lists the enzyme column name. The third column, cofactor describes the cofactor dependency for all the sequences (usually from different organisms) listed in the database BRENDA for this EC number entry. NADH (respectively NADPH) means that all the records are listed as being NADH (respectively NADPH) dependent. NAD(P)H means that there are records of sequences using either one of the two for this particular EC number. The fourth and last column lists the PDB code of the structural representative that was manually selected after literature review.

DETAILED DESCRIPTION

A. Overview

Figure 1:
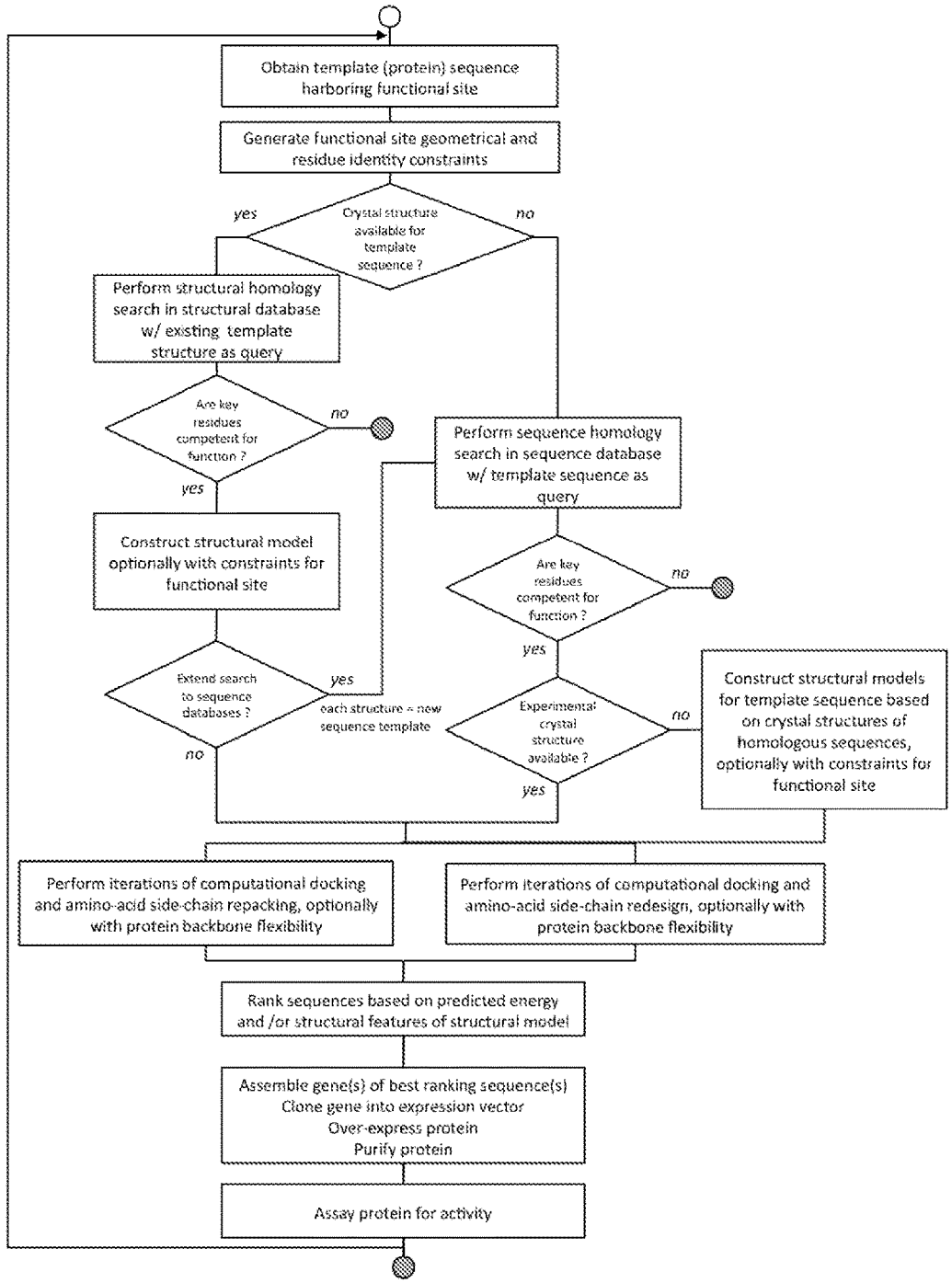
FIG. 1 represents the flow of operations occurring during application of one embodiment of the invention. Open circle represents the start of the operation flow. Diamond boxes are steps in the operation flow where a decision has to be made, either in the software flow (i.e., an automated choice) or by the operator running the software. Closed circles represent the end of the operation flow.

In various embodiments, the computational methods contemplated herein are used for automaticallyengineering, obtaining, making, indentifying, screening for and/or optionally designing a protein with either protein-protein binding function (i.e., proteins binding a specific polypeptide), protein ribonucleotide binding function, small molecule binding function as well as enzymatic activity (i.e., protein catalyzing a chemical reaction). In one embodiment, the computational methods contemplated herein comprise at least a coarse-grained structural model of the ligand(s) or transition state(s) that is used in the structural model evaluation, e.g., computational docking of the ligand(s), substrate(s), transition state(s) and/or products and computational redesign. One non-limiting example of such coarsegrain models for a protein ligand and a small-molecule ligand can be found in Rohl et al., *Protein Structure Prediction Using Rosetta, Meth. in Enzymology* 383:66-93 (2004) and Davis et al., *RosettaLigand Docking with Full Ligand and Receptor Flexibility, JMB* 385:381-392 (2009) respectively.

In various embodiments, the present invention provides for methods for discovering and/or making and/or designing having one or more desired characteristics. Without wising to be bound to any particular theory, the present invention contemplates, in part, that the inventive automated computational protein design methods contemplated herein can be used to design a protein with any desired functionality including, but not limited to, ligand binding, enzymatic activity, catalytic activity, substrate specificity, regioselectivity and/or stereoselectivity, or any suitable combination thereof.

In particular embodiments, a method of making, obtaining, or screening for one or more proteins comprises: preparing a functional site description based on at least one three-dimensional protein structure having the desired function or an analogous function, or having structural or sequence homology to a protein with the desired function or analogous function; computationally selecting a set of amino acid sequences having structural homology and/or sequence homology to the structure three-dimensional protein, providing a structural model for each said amino acid sequence, and selecting the amino acid sequences satisfying the functional site description; recombinantly expressing or by assaying the protein as expressed in its original host organism and confirming the desired function for at least one amino acid sequence, thereby identifying a protein having the desired function; and producing the protein having the desired function in a host cell or in vitro translation system.

In particular embodiments, the desired function is binding to one, two, three, four, five, or more ligands. Illustrative examples of suitable ligands for which proteins can be computationally designed or selected or screened for to bind include, but are not limited to, small molecules, hormones, proteins or peptides, cytokines, growth factors, transcription factors (activators or repressors), epigenetic modulators, saccharides, oligosaccharide, polysaccharides, fatty acids, nucleotides, ribonucleotides, deoxyribonucleotides, tRNAs, shRNAs, miRNAs, snoRNAs, piRNAs, aptamers, or synthetic polymers.

In particular embodiments, the methods contemplated herein are used to design, make, obtain, screen for, or identify a protein comprising one or more desired enzymatic or catalytic activities. Without wishing to be bound to any particular theory, it is contemplated that the methods disclosed herein can be used to obtain or produce and/or design a protein comprising any enzymatic activity. Illustrative, non-limiting, examples of enzymatic activities suitable for which proteins can be designed include oxidoreductases, transferases, hydrolases, lyases, isomerases and ligases including, but are not limited to dehydrogenase activity, carbonyl reductase activity, decarboxylase activity, glycosidase activity, glucosidase activity, beta-lactamase activity, aldolase and retro-aldolase activity, dehydratase activity, CoA-transferase activity, ene reductases, terpene synthase, deaminase activity, and the like.

In a certain embodiment, the methods contemplated herein are used to design a dehydrogenase, carbonyl reductase, decarboxylase, glycosidase, glucosidase, or a beta-lactamase.

Additionally, if the proteins made or identified by the methods contemplated herein comprise an enzymatic activity, the desired functionality optionally may include substrate specificity or selectivity, a regioselectivity and/or a stereoselectivity. In particular embodiments, an enzyme has "substrate specificity," "substrate selectivity," and/or stereoselectivity if the desired characteristic is greater than the background, about 5% greater than background, about 10% greater than background, about 10% greater than background, about 15% greater than background, about 20% greater than background, about 25% greater than background, about 30% greater than background, about 35% greater than background, about 40% greater than background, about 40% greater than background, about 45% greater than background, about 1.5 times greater than background, 2 times greater than background, about 5 times greater than background, about 10 times greater than background, about 20 times greater than background, about 50 times greater than background, about 100 times greater than background, or about 1000 times greater than background or more.

In one embodiment, the enzyme is a dehydrogenase or carbonyl reductase. In another embodiment, the enzyme is a decarboxylase. In yet another embodiment, the enzyme is a glycosidase or glucosidase. In one embodiment, the enzyme is a beta-lactamase.

In particular embodiments, one or more amino acid sequences are selected that have amino acid identit(ies) and corresponding geometric placement(s) that sufficiently correspond to a functional site of a contemplated enzyme. The amino acid sequences that satisfy a functional site description may be selected by various methods, including but not limited to, docking a ligand or substrate(s), transition state, or reaction product(s) relating to the desired function.

Illustrative examples of suitable functional site descriptions include, but are not limited to one or more of: a structural model of one or more of ligands, reaction substrate(s), transition state(s), and reaction product(s); amino acid identities for each functional site amino acid residue, rotameric states for each functional residue, rotameric states for each substrate, rotameric states for each ligand, rotameric states for each transition state, rotameric states for each reaction product, and geometric placement of the functional residues with respect to said reaction substrate(s), transition state(s), and/or reaction product(s).

In particular embodiments, functional site descriptions include, but are not limited to, amino acid identities for each functional site amino acid residue, rotameric states for each functional residue, rotameric states for each ligand, and geometric placement of the functional residues with respect to said ligands.

Various computational methods exist in the art that enable the skilled artisan to construct a functional site description. Illustrative examples of such computational tools include, but are not limited to one or more of quantum mechanical calculations, molecular mechanics, molecular dynamics, and human intuition, or a suitable combination thereof.

In various embodiments, the skilled artisan may use various art-known methods to derive the three dimensional structure of a protein, including but not limited to x-ray crystallography, nuclear magnetic resonance, or electron scattering or diffraction, or may find such a preexisting such three dimensional structure in a public or private structural database.

In particular embodiments, the three-dimensional protein structure includes one or more of a ligand(s), reaction substrate(s), or reaction product(s) in the functional site.

In one embodiment, the three-dimensional structure has structural or sequence homology to a protein having the desired function or analogous function. In a particular embodiment, the sequence homology at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%, including any intervening percentage of homology.

In a certain embodiment, the structural homology is optionally at most 5.0 angstrom (Å) root mean square deviation (RMSD) over the functional residues, at most 5.0 Å RMSD over at least 25% of the structure, at most 5.0 Å RMSD over at least 30% of the structure, at most 5.0 Å RMSD over at least 35% of the structure, at most 5.0 Å RMSD over at least 40% of the structure, at most 5.0 Å

RMSD over at least 45% of the structure, or at most 5.0 Å RMSD over at least 50% of the structure.

In particular embodiments, the analogous function is selected from a second ligand or group of ligands comprising a common core. For instance, (see Example 4), the analogous function can be that of a dehydrogenase enzyme oxidizing 3-hydroxybutyrate (where the carbonyl being oxidized is at position 3), whereas the desired function is the oxidation of the carbonyl at position 4 in 4-hydroxy-2-oxopentanoic acid. In this case, the common core between the two ligands is the carbonyl functional group on a linear carbon chain. In a certain embodiment, the analogous function is the same or substantially the same enzymatic activity on a different substrate.

In various embodiments, the computational enzyme design methods contemplated herein used structural homology modeling to identify suitable candidate amino acid sequences to be used in the design for a protein having a desired activity. Illustrative examples of structural alignment software that can be used to select suitable amino acid sequences by structural homology include, but are note limited to, MAMMOTH/MAMMOTH-mult, CE/CE-MC, FATCAT/jFatCat, DALI/DaliLite, FAST, EXPRESSO, TopoFit, MUSTANG, GANGSTA/GANGSTA+, ProFit, SABERTOOTH. Alternatively, structural protein and protein domain classification databases such as SCOP, DALI-database, Pfam, CATH, TOPOFIT-DB, as well as any database constructed using structural alignment software such as that listed above, can be used to obtain structural homologous sequence to a query sequence.

In various embodiments, the computational enzyme design methods contemplated herein used sequence-based homology modeling to identify suitable candidate amino acid sequences (or nucleic acids encoding the same) to be used in the design for a protein having a desired activity. Illustrative examples of structural alignment software that can be used to select suitable amino acid sequences by sequence homology include, but are not limited to, BLASTP, PSI-BLAST, DELTA-BLAST, OR HMMER, JackHMMER.

In particular embodiments, selecting a suitable amino acid sequence comprises scoring the amino acid sequences by computationally docking the ligand, and optimizing the positioning of the amino acid side chain and main chain atoms by minimizing the energy of the ligand(s)/transition state(s)-structure interaction, the protein structure energy and/or by minimizing the free energy of ligand(s)/transition state(s).

In certain embodiments, docking the ligand comprises positioning of the ligand in the functional site, with one or more of: protein side chain repacking, optimizing the position of the protein side-chain and main-chain atoms, and optimizing the ligand internal degrees of freedom by minimizing the energy of the ligand(s)/transition state(s)-structure interaction, the protein structure energy and/or by minimizing the free energy of ligand(s)/transition state(s).

In one embodiment, the amino acid sequences are scored by computationally docking the reaction substrate(s), transition state(s), or reaction product(s), and optimizing the positioning of the amino acid side chain and main chain atoms by minimizing the energy of the ligand(s)/transition state(s)-structure interaction, the protein structure energy and/or by minimizing the free energy of ligand(s)/transition state(s).

In particular embodiments, the energy of the transition state complex is minimized while enforcing one or more constraints on the protein structure. In one embodiment, the structure of the protein is constrained to restrict or enforce the movement of the protein backbone or amino-acid sidechains to a particular region of space or to a particular range of internal geometries. In related embodiments, the constraints are assigned to the relevant ligands to enforce the proper geometry necessary for function, optionally wherein the proper geometry is the binding site or active site geometry.

In one embodiment, docking the reaction substrate(s), transition state(s), and/or reaction product(s) comprises positioning of a model of the reaction substrate(s), transition state(s), and/or reaction product(s) in the functional site, with one or more of: protein side chain repacking, optimizing the position of the protein side chain and main chain atoms, and optimization of the internal degrees of freedom of the ligand, reaction substrate(s), transition state(s), and/or reaction product(s) by minimizing the energy of the ligand(s)/transition state(s)-structure interaction, the protein structure energy and/or by minimizing free energy of ligand(s)/transition state(s). Suitable constraints that can be placed on the amino acid sequence and ligands, substrate(s), transition state(s) and/or reaction product(s) to minimize the free energy of the of the ligand-structure interaction, the protein structure and/or minimizing the free energy of the transition state include, but are not limited to: geometrical constraints used to define and enforce the relative positioning of functional catalytic residues to the substrate(s), transition state(s) and/or product(s), constraints enforcing particular internal geometries (such as specific conformers and rotameric states) in the substrate(s), transition state(s) and/or reaction product(s), as well as geometrical constraints used to define and enforce the relative or absolute positioning of both mainchain and sidechain atoms of part or all residues in the protein sequence (such as for instances constraints on the relative position of C$\alpha$ atoms between different residues, or constraints on the rotameric state and $\chi$ angle that can be adopted by protein residue sidechains, alone or with respect to other protein residues).

In particular embodiments, the amino acid sequence of the computationally designed protein is altered to minimize the energy of the ligand(s)/transition state(s)-structure interaction, the protein structure energy and/or by minimizing free energy of ligand(s)/transition state(s). Suitable constraints that can be placed on the amino acid sequence and substrate(s), transition state(s) and/or reaction product(s) to minimize the free energy of the of the ligand-structure interaction, the protein structure and/or minimizing the free energy of the transition state include, but are not limited to: geometrical constraints used to define and enforce the relative positioning of functional catalytic residues to the substrate(s), transition state(s) and/or product(s), constraints enforcing particular internal geometries (such as specific conformers and rotameric states) in the substrate(s), transition state(s) and/or reaction product(s), as well as geometrical constraints used to define and enforce the relative or absolute positioning of both mainchain and sidechain atoms of part or all residues in the protein sequence (such as for instances constraints on the relative position of C$\alpha$ atoms between different residues, or constraints on the rotameric state and $\chi$ angle that can be adopted by protein residue sidechains, alone or with respect to other protein residues).

In various embodiments, the present invention provides an iterative process for identifying or designing a protein having a desired functional characteristic. The iterations may include one or more, e.g., 1, 2, 3, 4, 5, 6, 7, 8, 9, 10 or more cycles of rigid-body positioning of the ligand/substrate/transition state(s)/product(s) with or without simultaneous protein side-chain repacking, discrete and/or continuous optimization of the protein side-chain and main-chain atoms, as well as discrete and/or continuous optimization of the ligand/substrate/transition state(s)/product(s) internal degrees of freedom, optionally in the presence of constraints as described elsewhere herein.

In various embodiments, the present invention provides an iterative method that may include one or more, e.g., 1, 2, 3, 4, 5, 6, 7, 8, 9, 10 or more cycles of computational redesign of the wild-type amino-acid sequence is carried out, preferably through one or more iterations between computational docking and computational redesign, to obtain new sequences predicted to have the desired function. Optionally, the amino acid sequences selected after optimization of the protein structure model as described previously using fragment insertion, backbone perturbation, sidechain rotamer optimization, and minimization.

In particular embodiments, homology models of the sequence homologs are constructed based on one or more three-dimensional protein structure template (s). Software can be designed to perform such modeling or existing modeling software including, but not limited to, ROSETTA, ROBETTA, TASSER, I-TASSER, HHpred, HHsearch, or MODELLER, or SWISS-MODEL, can be used to build the sequence homology models.

In various embodiments, one or more sequence or structural homologs have less than 90% amino acid sequence identity, less than 85% amino acid sequence identity, less than 80% amino acid sequence identity, less than 75% amino acid sequence identity, less than 70% amino acid sequence identity, less than 65% amino acid sequence identity, less than 60% amino acid sequence identity, less than 55% amino acid sequence identity, less than 50% amino acid sequence identity, less than 45% amino acid sequence identity, less than 40% amino acid sequence identity, less than 35% amino acid sequence identity, less than 30% amino acid sequence identity, less than 25% amino acid sequence identity, or less amino acid sequence identity to the amino acid sequence of the three-dimensional protein structure.

In particular embodiments one or more sequence or structural homologs have between 10 and 25% amino acid sequence identity, between 10 and 30% amino acid sequence identity, between 10 and 40% amino acid sequence identity, between 10 and 50% amino acid sequence identity, between 25 and 50% amino acid sequence identity, between 10 and 30% amino acid sequence identity, between 25 and 75% amino acid sequence identity, between 30 and 50% amino acid sequence identity, between 30 and 80% amino acid sequence identity to the amino acid sequence of the three-dimensional protein structure.

In particular embodiments, the method is used iteratively. In one embodiment, a protein structure is first used to make a set of sequences (either selected or designed) as described elsewhere herein. Since all the sequences produced by this first iteration of the method originates from structural models, the structures can be used as new starting structures for another, second iteration of the method. Optionally, only the structures of the sequences that have been made, tested experimentally, and for which the desired function has been validated are used as new templates for another iteration of a method contemplated herein. Optionally, only the structures of the sequences that have been made, tested experimentally and for which a function analogous to the desired function has been validated are used as new templates for another iteration of a method contemplated herein.

In a particular embodiment, where the structural models are obtained by homology modeling or threading during the course of the first iteration as described elsewhere herein, experimentally derived protein structures (for instance through X-ray crystallography, NMR-spectroscopy or electron microscopy) are obtained, optionally only for the sequences after the first iteration that were validated to have the desired, or an analogous, function, and these experimentally derived structures used as starting structures for the second iteration, instead or in addition to the structural models generated computationally. Each structure can be used individually as a starting structure for the second iteration, or they can be grouped in subclasses that are sufficiently close to each other and only one representative for each class used as starting structure for the second iteration. In turn, the structures resulting from applying the method in the second iteration can be used as starting structures for another, third iteration of a method contemplated herein. Thus, in certain embodiments, the method can be applied iteratively, e.g., can be performed for one, two, three, four, five, six, seven, eight, nine, ten, 15, 20, 25, 30, 35, 40, 45, 50, 100 or more iterations, or until convergence occurs.

In a preferred embodiment, the methods contemplated herein track all the sequences generated in previous iterations, for example in a database, and iterations are stopped when additional iterations fail to produce any new sequence when compared to the sequences generated in the previous iteration (in that case, we say the iterations have converged). Without wishing to be bound to any particular theory, because of the inherent stochasticity of docking and design, in certain embodiments, it may not be enough to stop as soon as an iteration fails to identify any new sequences. Instead, in particular embodiments, it is preferable to continue iterating for a sufficient number of iterations as to have a high probability that the method has actually converged. For example and typically, if no new sequences are generated after 10 or 50 iterations, it is likely that the method is converged.

In particular embodiments, amino acid sequences often require multiple rounds of design and optimization in order to obtain or produce a protein having the desired functional activity. In certain embodiments, wherein further function or functional activity is desired, the amino acid sequence having the desired function is subjected to directed evolution, random mutagenesis, and/or rational mutagenesis to improve the functional activity.

All publications, patents and patent applications cited herein are hereby incorporated by reference in their entirety.
B. Structural-Based Ligand/Transition State/Substrate/Product Modeling In various embodiments for identification and/or design of new enzymes, structural models of ligand(s), substrate(s), and/or transition state(s) along the reaction coordinate, and/or product(s) may be used, in the same fashion as disclosed in patents U.S. Pat. No. 7,574,306 and U.S. Pat. No. 8,340,951 and US20120100594, which are incorporated herein by reference in their entirety. Preferably structural models for all substrate(s), transition state(s) and product(s) are provided. Substrate and product models are typically generated using state-of-art small-molecule building software including, but not limited to, SPARTAN, Avogadro (Hanwell et al., *Avogadro: An advanced semantic chemical editor, visualization, and analysis platform, J. Cheiminform.* 4(1):17 (2012)) and Pymol, using equilibrium geometries for bond length, angles, dihedral angles and atom radii. In a preferred embodiment, the energy of the structures obtained are further minimized using a molecular mechanics force-field such as, but not limited to, MMF94 (Halgren, *II.*

MMFF94 *van der Waals and Electrostatic Parameters for Intermolecular Interactions, J. Comput. Chem.* 17: 520-552 (1996)), AMBER (Case et al., *The Amber biomolecular simulation programs, J.Comput Chem.* 26(16):1668-1688 (2005)), CHARMM (Brooks et al., *CHARMM: The Biomolecular Simulation Program, J. Comput. Chem.* 30(10): 1545-1614 (2009)), Dreiding (Mayo et al., *Dreiding—A generic force-field for molecular simulations, J. Phys. Chem.* 94: 8897-909 (1990)), AMOEBA (Ponder et al., *Current Status of the AMOEBA Polarizable Force-Field, J. Phys. Chem.* 114(8):2549-2564 (2010)) or the ROSETTA force-field (cited infra) and their final minimized energy recorded. In a particular embodiment, quantum mechanical calculations are performed to obtain one of multiple structural models of the ligands(s), substrate(s), transition state(s) and product(s) using quantum chemistry software packages such as, but not limited to, SPARTAN, Gaussian (Frisch et al., Gaussian 03 (Gaussian, Inc., Wallingford, Conn., 2003)), Jaguar (*Computational Chemistry*, David Young, Wiley-Interscience, 2001. Appendix A. A.2.5 pg 337, Jaguar) or GAMESS (Schmidt et al., *General atomic and molecular electronic structure system, Journal of Computational Chemistry* 14 (11): 1347-1363 (1003)). In particular embodiments, subsequent structural free energy minimization may be carried out with molecular mechanics force-field as described elsewhere herein.

Transition state(s) along the reaction pathway are not, by definition, equilibrium structures and thus cannot be generated using equilibrium values for bond lengths, angles, dihedral angles, as well as atom radii and charges. In particular embodiments, initial structural models of one or several transition state structures may be obtained from chemical intuition from the user. In this case, typical bond length, angles, dihedral angles, atom radii, charges and types found in similar known transition state structures for similar chemical reactions can be used. For example, the tetrahedral geometry characteristic of a nucleophilic attack of an activated hydroxyl to an electrophilic carbon (see Example 2) can be derived from experimental values obtained from protease and esterases studies, such as these relying on chemical inhibitor binding in the active site of these enzymes. In a preferred embodiment, structural models of one or several transition state structures are obtained through quantum chemical computations (such structure referred to as theozyme), as for example described in Tantillo et al., *Theozyme and Compuzymes: Theoretical Models for Biological Catalysis, Curr. Opin. Chem. Biol.* 2:743-750 (1998). Typically, the course of one chemical reaction is simulated along one reaction coordinate, yielding "snapshots" along the reaction path, and quantum mechanical calculations are carried out to estimate the molecular orbitals and enthalpy of the system. This allows the definition of one or multiple transition state(s), and for each such transition state, of a set of detailed structural models called transition structures.

Figure 4:
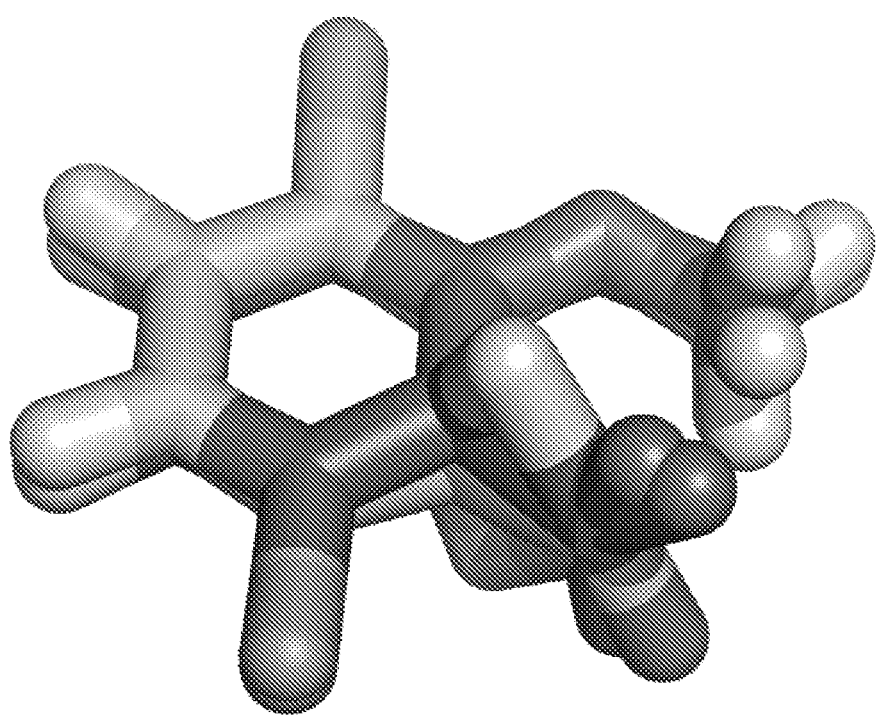
FIG. 4 depicts an ensemble of structural models of the transition state for the reaction. This ensemble is subsequently used for docking and/or redesign of sequence or structure homologs. This corresponds to the structural models of ligands, and in the case of enzyme structural models of one or multiple transition state(s) along the reaction catalyzed, and/or structural models of reaction product(s). This particular ensemble has been generated with a specifically modified version of the small-molecule software OpenBabel, using the MMFF94 force-field. Constraints were placed on all bonds and angle to account for non-equilibrium geometries in the starting transition state structure, and conformers were generated that after 10,000 conjugate gradient minimization steps had a predicted energy of at most 2.8 kcal/mol higher than the minimized input transition state structure.

In some cases, the structures generated by application of the methods contemplated herein, have degrees of freedom that can be varied without affecting the total energy of the molecule or affecting it marginally. That is, a transition state along the reaction coordinate is represented by a discrete set or continuous ensemble of transition structures with different discrete or continuous values for a set of bond lengths, angles or dihedral angles. For example it is well known that butane can adopt three different conformational isomers (i.e. conformers), gauche, anti and eclipsed, with enthalpies that are within 0.9 kcal/mol. Therefore, all three conformational isomers can exist, for instance in aqueous solution at room temperature. For transition states, the reactive core of the molecule is constrained routinely, whereas several sidechains of the small molecule can have multiple conformers that are all compatible with the reaction proceeding. For example, in FIG. 4, FIG. 10 and FIG. 18, part of the molecule is constrained but a large number of conformers can exist in the transition state. In one embodiment, conformers of substrate(s), product(s) and transition state(s) are manually constructed. In a preferred embodiment, structural models of such conformers are automatically generated using a software program.

In one embodiment, a software component first reads each structural model files generated as described supra and elsewhere herein. Using file format translation tools including, but not limited to, the open-source OpenBabel (O'Boyle et al., *Open Babel: An open chemical toolbox, J. Cheminf.* 3:33 (2011)) or the commercial software OMEGA by OpenEye (Kirchmair et al., *Comparative Performance Assessment of the Conformational Model Generators Omega and Catalyst: A Large-Scale Survey on the Retrieval of Protein-Bound Ligand Conformations, J. Chem. Inf. Model.* 46 (4):1848-1861 (2006)), it is possible to read and write files in a wide variety of formats. Illustrative examples of file formats that are used are PDB, MOL and MOL2 formats.

In one embodiment, a program first performs conformational optimization of the total energy of the input molecule using a molecular mechanics force-field including, but not limited to, MMF94, AMBER, CHARMM, Dreiding, AMOEBA or the ROSETTA force-field, and a continuous optimization algorithm including, but not limited to, Powell's, DFP, BFGS (*Numerical Recipes: The Art of Scientific Computing, Third Edition* (2007)) sequential quadratic programming or interior point optimization. Optionally, constraints can be placed before optimization on bond lengths and angles to keep them as close as possible from their values in the input structural model. In particular embodiments, this feature is critical when generating ensemble of transition state structures; otherwise, optimization with most force-fields would bring the bond lengths and angles back to their equilibrium values. In one embodiment, the user provides, through a suitable configuration file or interface, a set of bond length and angles constraints that he/she wants to be applied before optimization.

After conformational optimization of the total energy of the input molecule, the software program builds internally a data-structure representing the atom types and connectivity of the molecule based on the input atom type for each atom and the initial Cartesian coordinates read from the structural model file. This is used to automatically determine all the dihedral angles that can be rotated to generate conformers. Based on atom types and an internal knowledgebase gathered from a large dataset of small-molecule conformation, the program then affects a set of possible values for each dihedral angle that can be rotated. Alternatively, the user provides, through a suitable configuration file or interface, a list values for all or part of the dihedral angles that can be rotated. A combinatorial enumeration step then generates all the possible conformers based on these discrete values. For every such conformer, conformational optimization is carried out as described supra. The final energy obtained at the end of said optimization step is compared to the final energy of the optimized input structure, and conformers for which the difference of said two energies is lower than a threshold (for instance, 2.8 kcal/mol) are accepted and optionally output in a suitable file format (such PDB, MOL or MOL2).

C. Definition of Functional Sites

Figure 5:
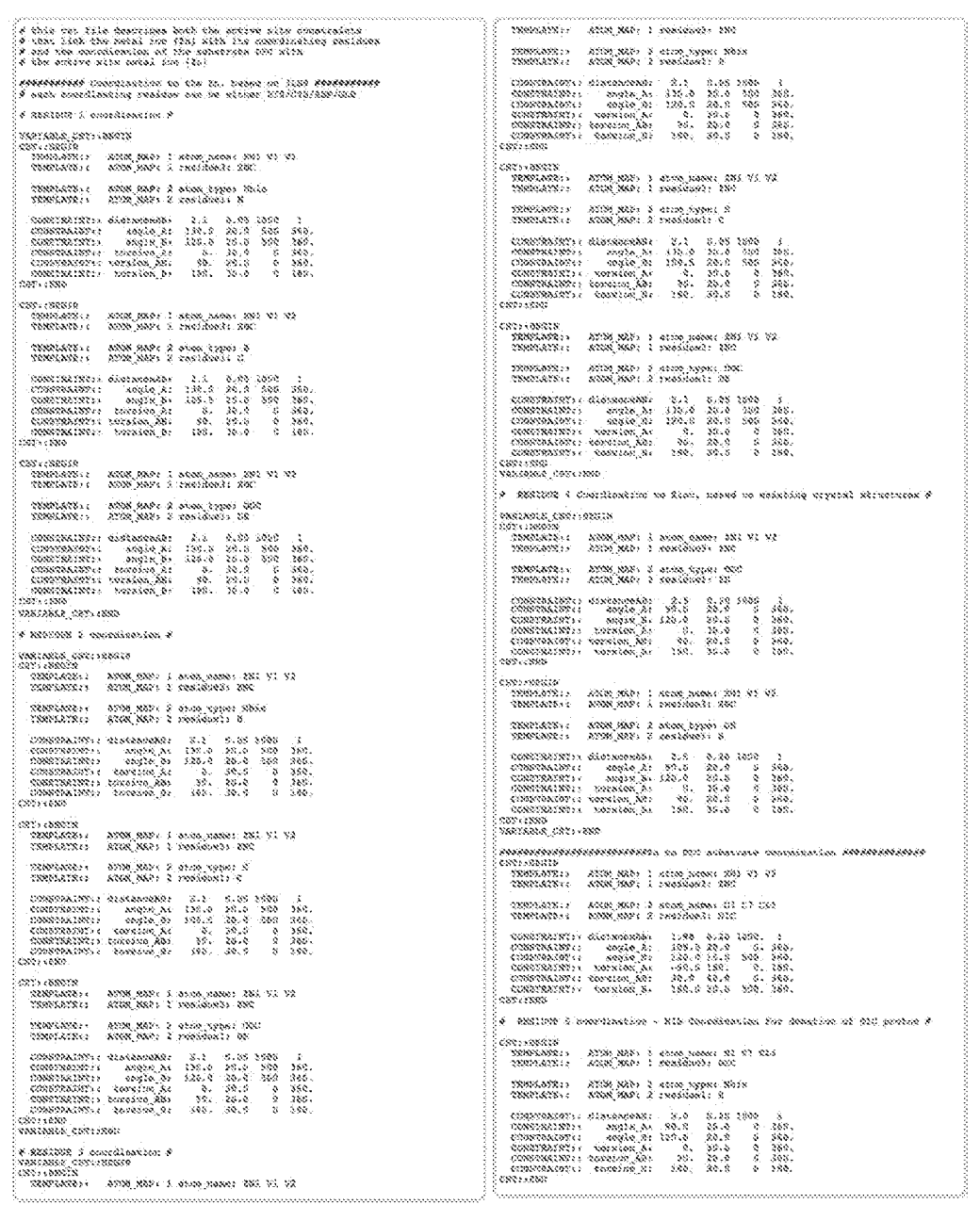

In addition to the structural models of the ligand(s), substrate(s), product and/or transition state(s), the definition of the functional site comprises the specification of the identities and potential rotameric states of key functional residues, as well as the definition of appropriate geometrical constraints used at various stages of the proposed method. The identities of the key functional residues can be specified as a list of names in a computer readable format, either on the command line or in a suitable computer file format. For instance, in the example of the identification of dicamba decarboxylases (Example 4), each of the key functional residues coordinating the zinc ion in the active site can be a Histidine but can also be a Cysteine and an Aspartate or a Glutamate residue. FIG. 5 provides an example of a file format where a list of block, separated by key words (VARIABLE_CST::BEGIN AND VARIABLE_CST:: END), which include the information of all possible functional residues (HIS(H)/CYS(C)/ASP(D)/GLU(E)).

Geometric constraints define the rigid-body placement of the substrate/product and/or transition state(s) structural model with respect to each functional residue. For example, in FIG. 5, three geometric constraints define the allowed range of rigid-body position of the zinc metal ion with respect to each functional histidine residue. An additional geometric constraint defines the relative position of the zinc ion to the dicamba molecule or transition state. Six degrees of freedom are necessary and sufficient to uniquely position in space a rigid-body with respect to a reference frame. There are multiple ways to choose said six degrees of freedom, and an example of parameterization well-suited to amino-acid residues and protein ligands is disclosed in patent U.S. Pat. No. 8,340,951, which is incorporated herein by reference in its entirety. The parameterization can be encoded in variety of computer file formats that can be used in the invention. See, e.g., FIG. 5. The keywords TEMPLATE::ATOM_MAP are used to specify 6 reference atoms (3 from the functional residue, 3 from the ligand, in this case the Zinc atom and additional "virtual" atoms) and the keywords CONSTRAINT::distanceAB, CONSTRAINT:: angle_A, CONSTRAINT::angle_B, CONSTRAINT::torsion_AB, CONSTRATIN::torsion_A and CONSTRAINT:: torsion_B specify the values of the six degrees of freedom, following the naming convention introduced in Zanghellini et al., *New algorithms and an in silico benchmark for computational enzyme design, Protein Sc.* 15:2785-2794 (2006). In some embodiments, one or more of the six degrees of freedom can adopt a discrete or continuous range of values (for instance, a dihedral angle can adopt the values $0, +\pi/2, -\pi/2, \pi$ radians, or could adopt any value between 0 and $\pi/2$ radians, or could be free to vary—that is, all values of the dihedral angle from 0 to $2\pi$ radians result in rigid-body placements of the structural model of the ligand(s), substrate(s), product and/or transition state(s) consistent with function).

D. Homology-Based Modeling

Techniques of homology modeling and threading are used to produce structural models to identify target sequences whose pre-existing three-dimensional structures are not available. These models may be used to evaluate the feasibility of the desired function, such as a chemical reaction or potential for binding the ligand(s), and may in addition by used as models to be used for further computational protein modeling and design techniques.

Homology modeling may comprise a variety of fixed and flexible backbone structural modeling techniques including, but not limited to, rotamer packing, whole structure minimization, rigid body minimization, loop modeling, backbone perturbation, fragment insertion, and constrained structure optimization. In particular embodiments, the choice of methods used is dependent on the degree of homology between the sequence in the template structure and each target sequence. For example, threading is used when the two sequences can be aligned without the introduction of gaps except at the N- or C-terminal of both sequences. For example, in threading, the template structure is equipped with the sequence of the query sequence, and the modeling may comprise iterating between amino-acid side-chain rotamer packing and whole structure minimization.

Initially, the sequence of the target protein is threaded onto an available template structure using either the alignment provided by a process detailed herein, or by an alignment made externally with either pairwise (such as, but not limited to, BLAST/PHI-BLAST, HMMER) or multiple alignment programs (such as, but not limited to, CLUSTAL/ CLUSTALW/Tcoffee), resulting in a starting model. Said starting model may be generated over multiple starting template structures. In a preferred embodiment, the structural models of the ligands/transition state(s)/substrate(s) and/or product(s) are positioned in the context of the starting model, in a manner consistent with the geometric constraints specified by the description of the functional site provided as a seed for the whole process as outlined elsewhere herein.

The residues in the target sequence are classified as to whether or not they are located in regions of the starting model where the protein backbone would have to be rebuilt. In particular embodiments, the alignment between the sequence of the template structure and the target sequence show deletion or insertions, as represented by at least one gap. When this is the case, the residue in the target sequence is said to require loop-modeling. In one embodiment, one or more residues in which an alignment does not exist with the template are classified as needing loop modeling, while other residues are classified as foregoing loop modeling. In a preferred embodiment of the invention, residues are further classified by looking at predicted secondary structure using secondary structures programs including, but not limited to, PSIPRED (Jones, *Protein secondary structure prediction based on position-specific scoring matrices, J. Mol. Biol.* 292:195-202 (1999)) and JUFO in a consensus fashion or single manner. If a non-aligned residue exists within a stretch of secondary structure predicted to be loop, then the residues within that loop are classified as needing loop modeling. In a preferred embodiment, residues are further classified by looking at their proximity to a set of residues either within the target sequence or external to the target sequence, such as the ligands themselves, as defined by the user. Residues within a user-defined distance of this set that have a corresponding aligned template residue are marked as foregoing loop modeling. In one embodiment, residues may be included or excluded from loop modeling based on criteria that include, but are not limited to, sequence distance from portions of the structure that are assigned as loop modeled by some prior criteria, Euclidean distance of loop take-off and landing points to atoms of other residues or other reference points, length of their predicted secondary structure elements, estimation of structural flexibility, and confidence in the template structure's coordinates. In a preferred embodiment, the user may specify one or more residues that will forego loop modeling regardless of any other criteria. In another embodiment, the residue classification may be selected in a randomized manner.

The homology modeling procedure incorporates constraints to restrict or enforce the movement of the protein backbone or amino-acid sidechains to a particular region of space. As used herein, the term "constraint" refers to the definition, usually in mathematical form, of one, multiple or a range of numerical value(s) that a geometric measure such as, but not limited to, a distance between two points or atoms, an angle between three points or atoms, or a dihedral between four points may adopt, whereas deviations from said specified value(s) result in a numerical or logical penalty. This prevents the structure from drifting too far from the starting template or losing proper geometry necessary for function, such as active site or binding site geometry.

Constraints may have varying mathematical functional forms, and may be formulated differently depending upon the region of the protein they are being assigned to. In a preferred embodiment, constraints are assigned with respect to the placed ligands to enforce the proper geometry necessary for function, such as the binding site or active site geometry. In one embodiment, this can be accomplished directly by using the constraint definition specified in functional site description as outlined elsewhere herein.

Alternatively, or in addition to, one or more residue atoms, such as Cα and Cβ atoms, participating directly in the functional site are mutually tethered to one another by constraints. In a preferred embodiment, one or more Cα atoms of residues in the active site or binding site and within a particular distance of the active site or binding site are tethered to the location of the Cα atom in the corresponding aligned template residue in three-dimensional Euclidean space by constraints. In one embodiment, one or more Cα atoms of residues that have an aligned residue in the template are mutually tethered to one another or to one, several, or many specific points in space to restrict their motion by constraints. In another embodiment, the user specifies constraints of particular mathematical functional forms over a user-defined set of residues or atoms to constrain the motion in addition to or independently of the automatically generated constraints.

In a particular embodiment, loop modeling is performed to model regions of the target sequence that are unaligned relative to the template or that appear to need large flexible backbone sampling as characterized by the classifications described elsewhere herein. Loop modeling is used to sample backbone configurations that have proper peptide backbone geometry, termed "closed," in loop modeling terminology. In a preferred embodiment, loop modeling is performed using a low resolution score function and sampling by a combination of fragment insertion and cyclic coordinate descent similar to the procedure described in Qian et al., *High-resolution structure prediction and the crystallographic phase problem*, Nature 405:259-274 (2007). In one preferred embodiment, the low resolution phase is followed by a phase of loop refinement with a high resolution scoring function and small backbone perturbations, minimization, and sidechain repacking similar to the procedure described in Wang et al., *Protein-protein docking with backbone flexibility*, J. Mol. Biol. 373:503-519 (2007). In another preferred embodiment, the loop modeling is performed by an analytical loop closure technique including, but not limited to, the procedure described in Mandell et al., *Sub-angstrom accuracy in protein loop reconstruction by robotics-inspired conformational sampling*, Nature Methods 6:551-552 (2009). In one embodiment, loop modeling is performed by an enumerative technique where backbone angles are sampled either continuously or in discrete intervals. In another embodiment, loop modeling is performed by a randomized algorithm technique where backbone angles are chosen randomly. In one embodiment, each loop region is modeled using a different technique depending upon loop length or other automatic or user specified criteria. In another embodiment, the loop modeling may be performed in the presence of the constraints described elsewhere herein.

In one embodiment, the piecewise optimization of non-loop modeled regions in the target is performed to allow minor rearrangements that may need to occur in the relative spatial orientation of said non-loop regions. In one preferred embodiment of the invention, this piecewise modeling is performed in the presence of constraints as described previously that may be up-weighted or down-weighted to allow smaller or larger motions in certain parts of the structure. In one embodiment, the piecewise modeling consists of iterating between minimization and side-chain rotamer optimization. In another embodiment, the piecewise modeling includes random perturbations to the relative spatial orientations of the parts of the structure.

E. Structural Optimization

As its name implies, the whole structure optimization stage of the target allows the entire target structure to be optimized all at once. In one embodiment, the whole structure optimization stage consists of a combination that may include, but are not limited to, fragment insertion, backbone perturbation, sidechain rotamer optimization, and minimization, similar to the procedures described in Simons et al., *Assembly of protein tertiary structures from fragments with similar local sequences using simulated annealing and Bayesian scoring functions*, J. Mol. Biol. 25:209-225 (1997), Rohl et al., *Protein structure prediction using Rosetta*, Methods Enzymol. 383:66-93 (2004), Raman et al., *Structure prediction for CASP8 with all-atom refinement using Rosetta*, Proteins 77:89-99 (2009), Eswar et al., *Protein structure modeling with MODELLER*, Methods Mol. Biol 426:145-159 (2008) and Leaver-Fay et al., *ROSETTA3, an object-oriented software suite for the simulation and design of macromolecules*, Methods in Enzymology 487:545-574 (2011). In a particular embodiment, continuous fragment optimization is employed instead of discrete fragment insertion, as described for instance in Hamelryck et al., *Sampling realistic protein conformations using local structural bias*, PLoS Comput. Biol. 2(9):e131 (2006) or Boomsma et al., *A generative probabilistic model of local protein structure*, PNAS 105(26):8932-7 (2008). In one embodiment, the whole structure optimization is performed in the presence of constraints as described elsewhere herein. In addition, the weights for the individual terms in the score function may be altered to allow for sampling in different regions of conformational space. In a particular embodiment, the optimization is performed without constraints and/or without spatially dependent score function weights.

F. Computational Docking and Redesign

In a particular embodiment, after one or several experimentally derived three-dimensional structures or homology-models have been obtained from sequence or structure alignment of the seed sequence or structure, computational docking of the structural models of the ligand(s), substrate(s) and/or product(s) and/or transition state(s) is performed, under the constraints specifying acceptable rigid-body position of the ligand(s), substrate(s), product(s) and/or transition state(s) with respect to the functional residue present in three-dimension structure of the protein. In one embodiment, the computational docking uses a stochastic algorithm such as Metropolis Monte Carlo, as described in Gray et al., *Protein-protein docking with simul-*

*taneous optimization of rigid-body displacement and side-chain conformations, Protein Sci.* 331:281-299 (2003).

In a certain embodiment, the computational docking uses deterministic algorithms such as grid-based Fast Fourier Transform methods as implemented for instance in the software package AUTODOCK, Morris et al., *Automated Docking Using a Lamarckian Genetic Algorithm and and Empirical Binding Free Energy Function, J. Computational Chemistry* 19:1639-1662 (1998). In a particular embodiment, the computational docking uses spherical-harmonic small-molecule docking, as described for instance in Cai et al., *Protein-ligand recognition using spherical harmonic molecular surfaces: towards a fast and efficient filter for large virtual throughput screening, J. Mol. Graph. Model.* 20(4):313-328 (2002) or in Perez-Nueno et al., *Using consensus-shape clustering to identify promiscuous ligands and protein targets and to choose the right query for shape-based virtual screening, J. Chem. Inf. Model.* 51(6):1233-1248 (2011). The scoring function may include terms used in small-molecule or polymer—protein docking, such as a Lennard-Jones potential, an implicit solvent solvation model, an explicit hydrogen-bonding potential, an explicit electrostatic interaction term (e.g, with a Coulombic functional form) or an implicit electrostatic interaction term (e.g. a pair term), as well statistically derived terms such as a Ramachandran term, a deviation from rotameric penalty function, a secondary structure pairing term (such as strand pairing, helix-helix coil pairing), secondary structure propensity terms and a reference energy (that captures for example the unfolded state reference energy). In addition, specific energy or penalty terms derived from the geometric constraints defined between the functional residues and the ligand(s)/substrate(s) and/or product(s) and/or transition state(s) structural models are included during docking to sample primarily rigid-body placements of such structural models that are compatible with the desired protein function as well as do not violate drastically protein stereochemistry.

In a preferred embodiment, iterative rigid-body perturbations of the ligand/substrate(s)/product(s)/transition state(s), amino-acid side-chain repacking and side-chain and main-chain atom minimization, are performed as to find lowest minima in the energy landscape. In a preferred embodiment, this iterative process is complemented with alteration of the protein backbone using backbone modeling as described above in the case of loop modeling for homology model generation.

In another embodiment, computational docking is performed in conjunction with at least one step of design, where the identity of protein residues (excluding functional residues) can be altered as to stabilize the resulting protein and/or provide additional favorable atomic contacts to the placed ligand(s)/substrate(s) and/or product(s) and/or transition state(s), and/or buttress the position of functional residues. The computational design technique and algorithms described in Zanghellini et al., *New algorithms and an in silico benchmark for computational enzyme design, Protein Sc.* 15:2785-2794 (2006) and disclosed in U.S. Pat. No. 8,340,951, which is incorporated herein by reference in its entirety, may be used. In a preferred embodiment, an iterative stochastic method is employed where cycles of computational docking as described elsewhere herein, are combined with one of more step of sequence selection (design), resulting in a final set of structural models with optimally or sub-optimally placed rigid-body placement of the ligand(s)/substrate(s) and/or product(s) and/or transition state(s) and a new sequence of amino-acid.

After the computational docking or computational docking and design steps are complete, the structural protein models (and hence their sequences) are ranked by score and/or structural features, and their amino-acid sequences selected for further experimental characterization. The score used for ranking structural models may comprise a Lennard-Jones potential, an implicit solvent solvation model, an explicit hydrogen-bonding potential, an explicit electrostatic interaction term (e.g, with a Coulombic functional form) or an implicit electrostatic interaction term (e.g., a pair term), as well statistically derived terms such as a Ramachandran term, a deviation from rotameric penalty function, a secondary structure pairing term (such as strand pairing, helix-helix coil pairing), secondary structure propensity terms and a reference energy (that captures for example the unfolded state reference energy). An example of such score function used in some implementation of the software ROSETTA can be found in Rohl et al., *Protein Structure Prediction Using Rosetta, Meth. in Enzymology* 383:66-93 (2004).

In particular embodiments, features used to select structural protein models may include, but are not limited to, chemical complementarity (i.e., how well the residues surrounding the ligand match the chemical characteristics of some of all the atoms of the ligand, for instance whether hydrophobic atoms in the ligand are in van der Waals contact or close to hydrophobic atoms originating from protein residues, and whether polar atoms are in the vicinity of polar atoms originating from protein residues), the number of hydrogen bonding donors and acceptors that are not satisfied in the ligand and protein residues, and shape complementarity metrics as described in Lawrence and Colman, *Shape complementarity at protein/protein interface, JMB* (1993) that assess the tightness of fit between the ligand and the protein binding pocket (the method has been applied for measuring protein/protein and small-molecule/protein shape complementarity in the software ROSETTA).

G. Expression and Assay of Protein Activity

Figure 6:
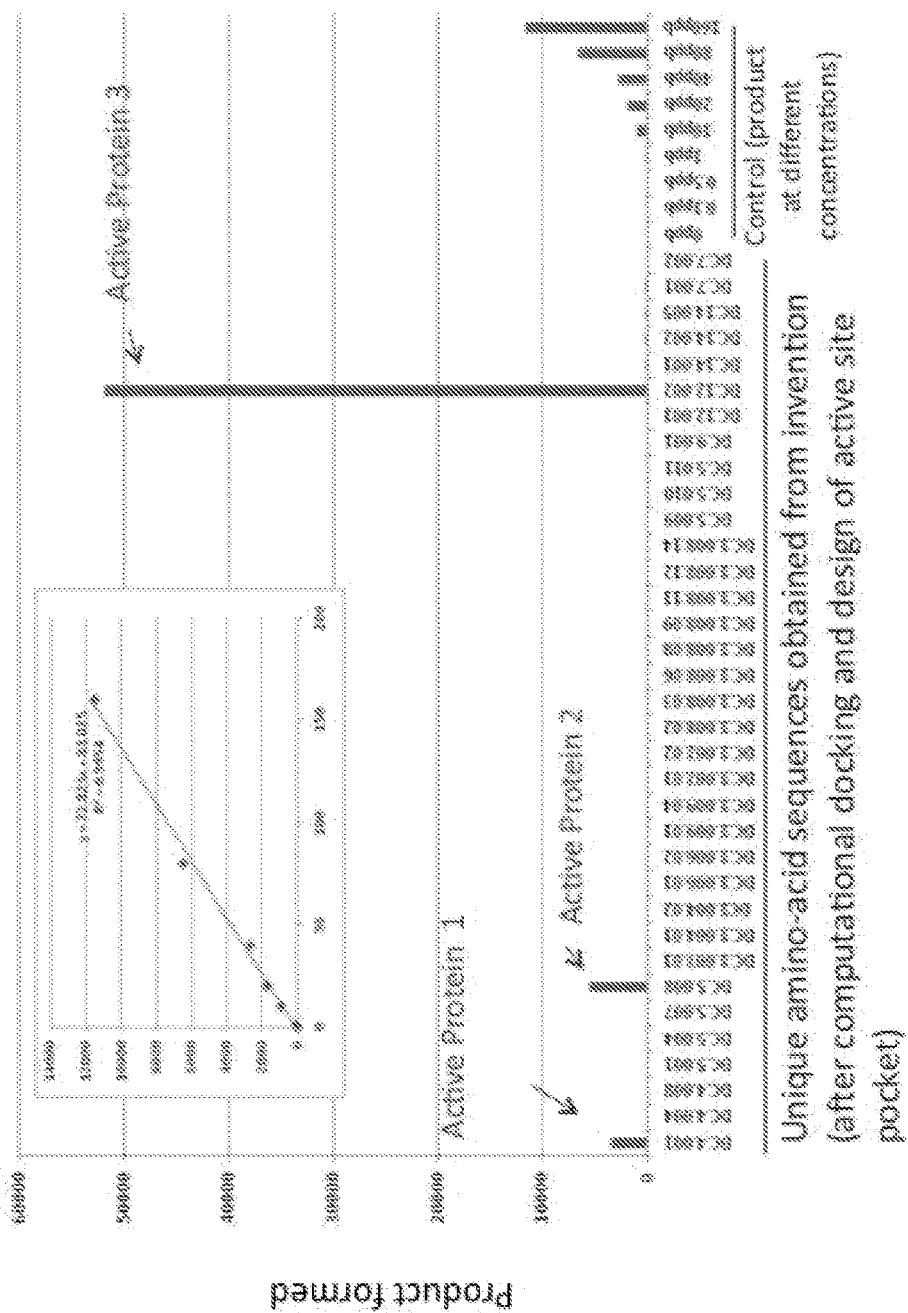
FIG. 6 shows experimental activity assay results for an ensemble of sequences that were obtained from the application of the invention to an enzyme target. In this case, the sequences correspond both to natural sequences found to be low scoring after transition-state docking (DC.4.001, DC.5.001, DC.7.001, DC.9.001, DC.12.001, DC.14.001), as well as sequences that were designed at the same time as the transition-state was docked as described elsewhere herein (all the other sequences such as the active DC.5.008, DC.12.002 or inactive DC.4.002, DC.5.007 . . . etc). The product formation is shown in y-axis, for each sequence id (shown in the x-axis). The controls (product levels spiked at increasing known concentrations) are on the right.

After one or more proteins have been identified, selected, and optionally designed, not all selected proteins may possess the desired functional activity. Accordingly, in various embodiments, the present invention contemplates, in part, expression the computationally selected and optionally designed proteins and assaying them for one or more desired functional activities. For instance, in Example 3 (see FIG. 6), 35 proteins were selected at the end of the process, the sequences were reverse-translated to DNA and codon optimized for expression in *E. Coli* and the corresponding gene assembled. The genes were cloned in pET-derived vectors with a 6-HIS purification tag, and the vectors transformed in competent BL21* or other DH5α *E. Coli* strains for overexpression. The overexpressed proteins were harvested after cell lysis and purified using a Ni-NTA column. The purified proteins were assayed using a GC/MS assay and 3 active proteins detected, exemplifying the efficacy of inventive computational methods contemplated herein. Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred embodiments of compositions, methods and materials are described herein. For the purposes of the present invention, the following terms are defined below.

The articles "a," "an," and "the" are used herein to refer to one or to more than one (i.e., to at least one) of the grammatical object of the article. By way of example, "an element" means one element or more than one element.

As used herein, the term "about" or "approximately" refers to a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length. In particular embodiments, the terms "about" or "approximately" when preceding a numerical value indicates the value plus or minus a range of 15%, 10%, 5%, or 1%.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

All publications, patent applications, and issued patents cited in this specification are herein incorporated by reference as if each individual publication, patent application, or issued patent were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1

Figure 7:
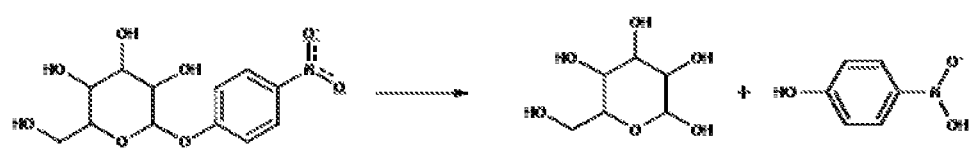
FIG. 7 depicts a beta-glucoside hydrolysis reaction, as can be catalyzed by beta-glycosidase enzymes, for the compound 4-Nitrophenyl alpha-D-galactopyranoside.

Computational Identification of Glucosidase Catalysing HE Hydrolysis of 4-Ntirophenyl α-D-Galactopyranoside In this example, the aim is to computationally identify sequences from a structural database that catalyze the hydrolysis of 4-nitrophenyl alpha-D-galactopyranoside (reaction depicted in FIG. 7) and predict the efficiency at which they will catalyze the reaction, so that the best enzymes for this substrate can be selected automatically. This example serves as the first benchmark demonstrating that the computational method disclosed here is capable of automatically predicting, in a set of sequences for which a crystal structure is available, which sequences will be catalyzing the desired reaction with the highest catalytic proficiency.

Figure 8:
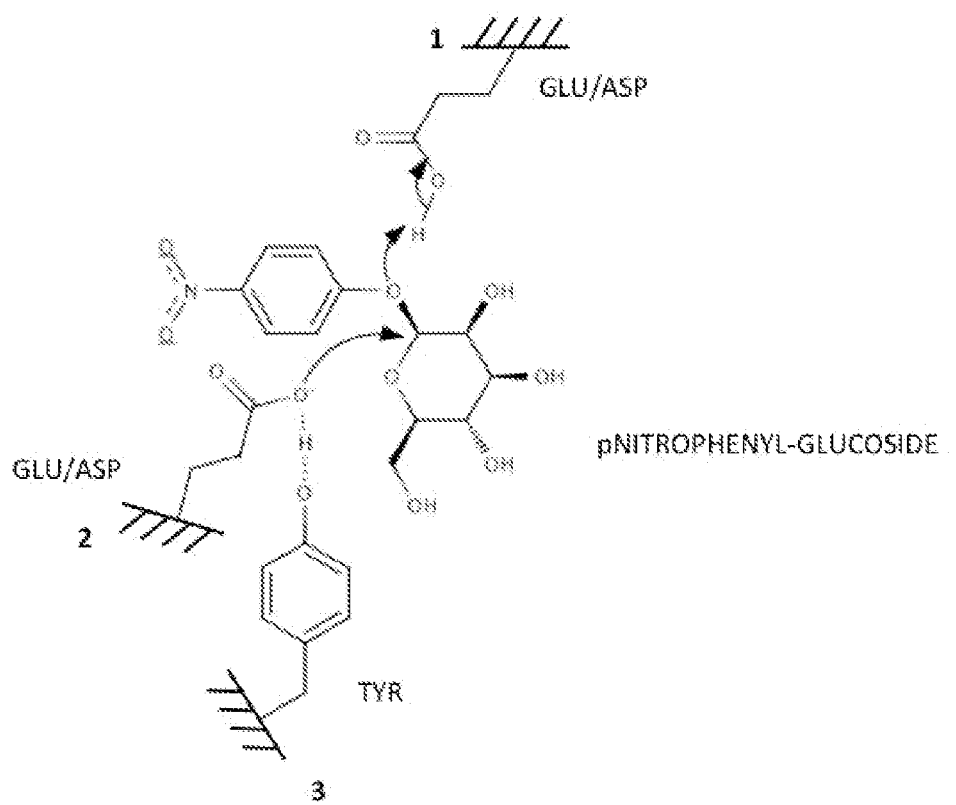
FIG. 8 shows the active site structure of beta-glucosidase enzymes (of the class EC 3.2.1.21). The modeled active site comprises three catalytic residues: catalytic residue 1 is an Aspartate or Glutamate residue, and protonates the oxygen on the leaving pnitrophenol group. One of the oxygen on catalytic residue 2, which is an Aspartate or Glutamate residue, acts as a nucleophile and attacks the sugar carbon C1.

As a template enzyme, the beta-glucosidase from Bacillus polymyxa (PDB ID 1e4i) was used. A high-resolution crystal structure for this enzyme was solved with the substrate analog 2-deoxy-2-fluoro-beta-d-glucosyl bound in the active site. From this sequence, a BLAST search on a non-redundant version of the sequences that are part of the protein data bank (PDB) yielded 10 crystal structures of different glycosidase enzymes with various degrees of sequence homologies (between 10 and 30% sequence identities). More glycosidases (including beta-glucosidases and other enzymes) were obtained from this BLAST search. However, the set of 10 structures was selected based on the availability of experimentally determined values for the catalytic parameters $k_{cat}$ and $K_M$ against the compound 4-nitrophenyl alpha-D-galactopyranoside. The selected 10 structures all harbor the same catalytic site, which is represented in FIG. 8.

Figure 10:
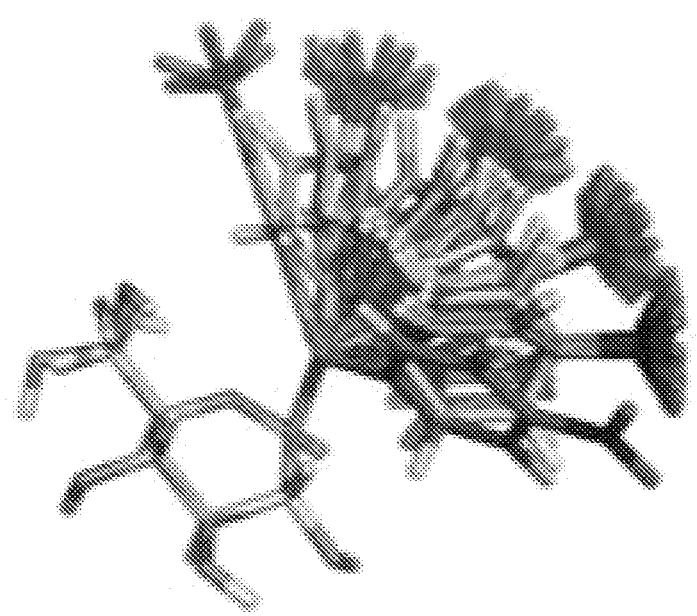
FIG. 10 shows the ensemble of transition structures built for the substrate depicted in FIG. 7, as described elsewhere herein. This particular ensemble has been generated with a specifically modified version of the small-molecule software OpenBabel, using the MMFF94 force-field. Constraints were placed on all bonds and angle to account for non-equilibrium geometries in the starting transition state structure, and conformers were generated that after 10,000 conjugate gradient minimization steps had an predicted energy of at most 2.8 kcal/mol higher than the minimized input transition state structure.
Figure 11:
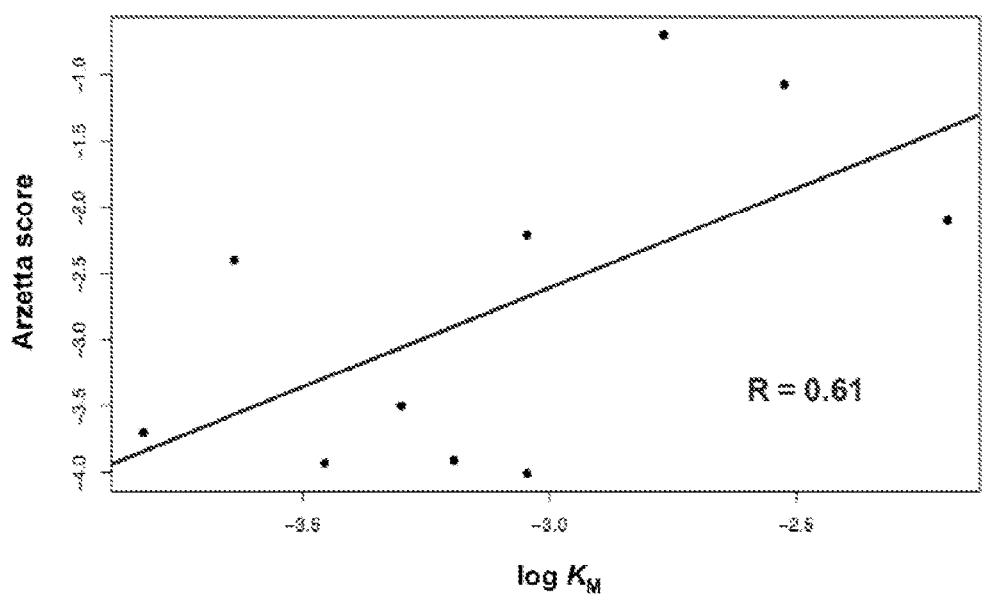
FIG. 11 represents the correlation between the experimental substrate binding values ($\log_e(KM)$, x-axis) and the value of the Rosetta scoring function (y-axis) for the lowest score obtained after constrained docking of the transition structures, for each of the 10 Glucosidase structures described in Example 1. The red line is the least-square fit corresponding to the reported correlation coefficient R of 0.61.

An ensemble of transition state structural models (transition structures) was first constructed in the program SPARTAN based on chemical analogs of the transition state for the reaction, and an ensemble of conformers were generated as described using a dedicated software derived from the software package and library OpenBabel, as described elsewhere herein. The resulting ensemble of structures is depicted in FIG. 10. Constraints between the three catalytic residues making up the functional site of all the glycosidases and glucosidase considered (one Aspartate or Glutatmate residues and one tyrosine residue) and the transition state structures were defined and encoded in a constraint file (see FIG. 9). The ensemble of the transition structures were computationally docked in each of the 10 experimentally derived crystal structure, under the constraints defined for the functional site, and the score for the best scoring transition structures in each of the 10 crystal structures were compared to the logarithm of the $K_M$ that was measured experimentally. The result, which can be found in FIG. 11, shows that the computed score correlates well (R=0.61) with the experimentally measures of $K_M$ demonstrating that the invention allows the automated selection ("identification") of sequences among a database of structures of the enzymes that will catalyze the hydrolysis of 4-nitrophenyl alpha-D-galactopyranoside.

Example 2

Figure 12:
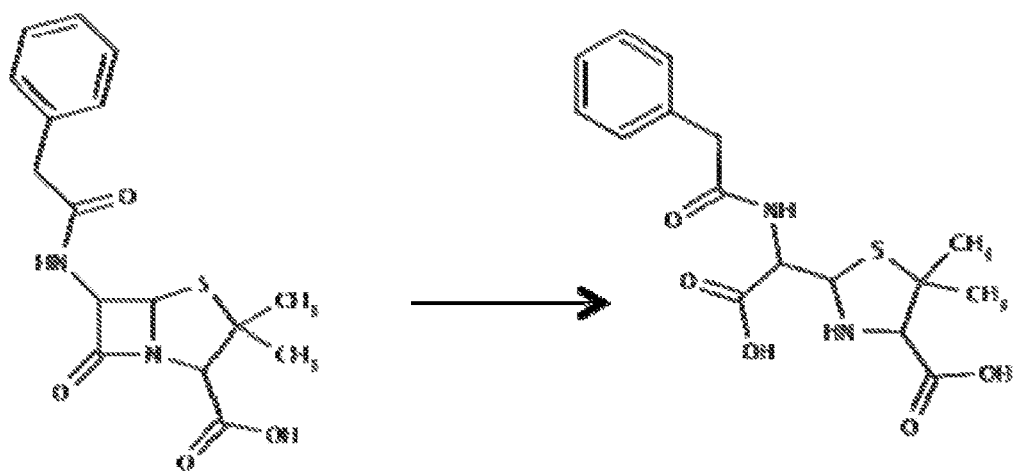
FIG. 12 depicts the hydrolysis reaction of benzyl-penicillin, an antibiotic of the lactam class. This is the reaction catalyzed for example by some class A, B or C bacterial beta-lactamase that provide antibiotic resistance to their host.

Computational Identification of Beta-Lactamase Sequences Catalysing the Hydrolysis of Benzl-Penicillin G In this example, the aim is to computationally identify sequences from a structural database that catalyze a different reaction: the hydrolysis (and inactivation) of the antibiotic molecule benzyl-penicillin g (reaction depicted in FIG. 12), and similarly to example 1 above, predict the efficiency at which each sequence will catalyze the reaction so that the best enzymes for this substrate can be selected automatically. This example serves as another benchmark demonstrating that the computational method disclosed here is capable of automatically predicting, in a set of sequences for which a crystal structure is available, which ones will be catalyzing the desired reaction with the highest catalytic proficiency.

Figure 13:
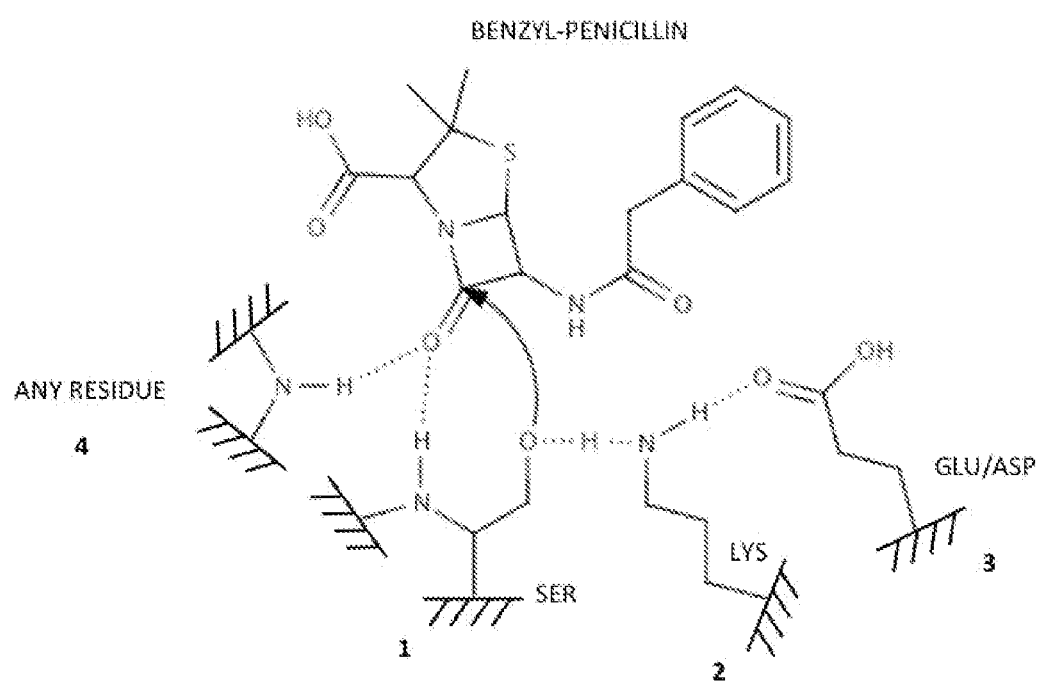
FIG. 13 shows the active site structure of class A and C beta-lactamase enzymes (of the class EC 3.5.2.6). The modeled active site comprises four catalytic residues: catalytic residue 1 is a conserved Serine residue that acts as a nucleophile to attack on the lactam ring of the substrate (see solid arrow). Catalytic residues 2 and 3, a conserved Lysine and Aspartate/Glutamate residue respectively, act as a proton channel to deprotonate the nucleophilic Serine. Finally, the backbone amide of catalytic residue 1 as well as the backbone amide of other residue, catalytic residue 4 (whose identity is not conserved) form an oxyanion hole that facilitates the nucleophilic attack of the catalytic Serine by stabilizing the developing negative charge on the lactam carbonyl oxygen.

Several bacterial beta-lactamase enzymes have been reported to degrade benzyl-penicillin, among other antibiotic possessing a lactam ring. Based on their catalytic sites and mechanisms of action, bacterial beta-lactamase have been divided into three different classes: class A, B and C. Class A and C both use a very similar active site, relying on a SER triad to enact a nucleophilic attack on the lactam ring of benzyl-penicillin g. Class B, on the contrary, relies on a different active site employing a Zinc binding site that activates the hydroxyl group from a water molecule to act as the nucleophile. A set of 19 class A and C beta-lactamase for which a high-resolution crystal structure was selected based on a literature search. For each of these 19 sequences, catalytic parameters $k_{cat}$ and $K_M$ for their activity against benzyl-penicillin g have been determined experimentally. All 19 structures share the same active site that is depicted in FIG. 13.

Figure 18:
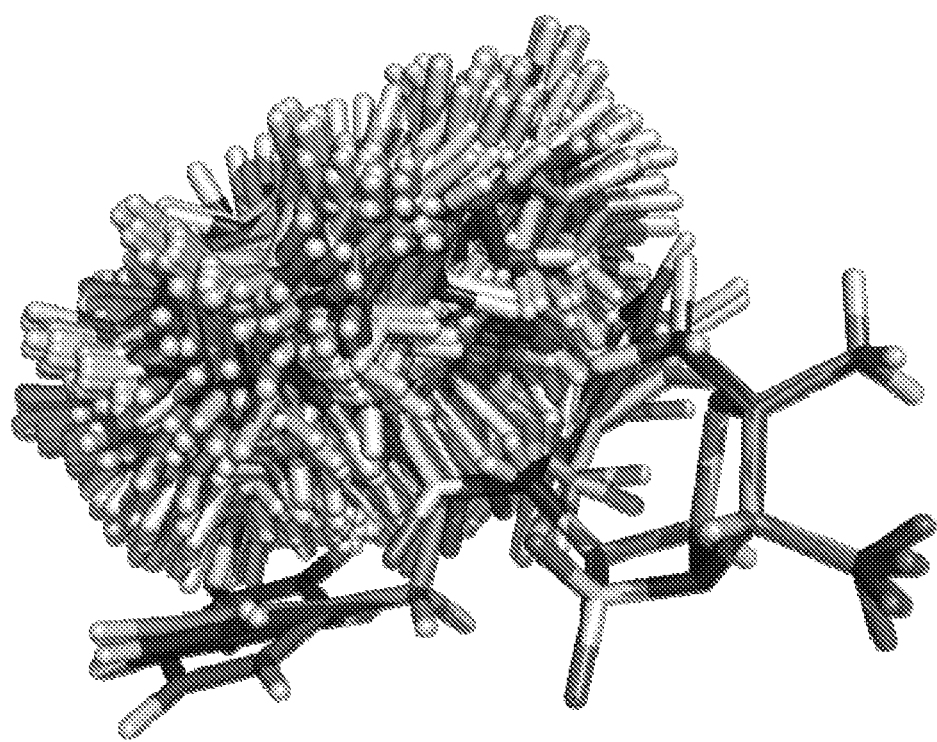
FIG. 18 shows the ensemble of transition structures built for the R stereoisomer of substrate depicted in FIG. 7, benzyl-penicillin, as described elsewhere herein. This particular ensemble has been generated with a specifically modified version of the small-molecule software OpenBabel, using the MMFF94 force-field. Constraints were placed on all bonds and angle to account for non-equilibrium geometries in the starting transition state structure, and conformers were generated that after 10,000 conjugate gradient minimization steps had an predicted energy of at most 2.8 kcal/mol higher than the minimized input transition state structure.
Figure 19:
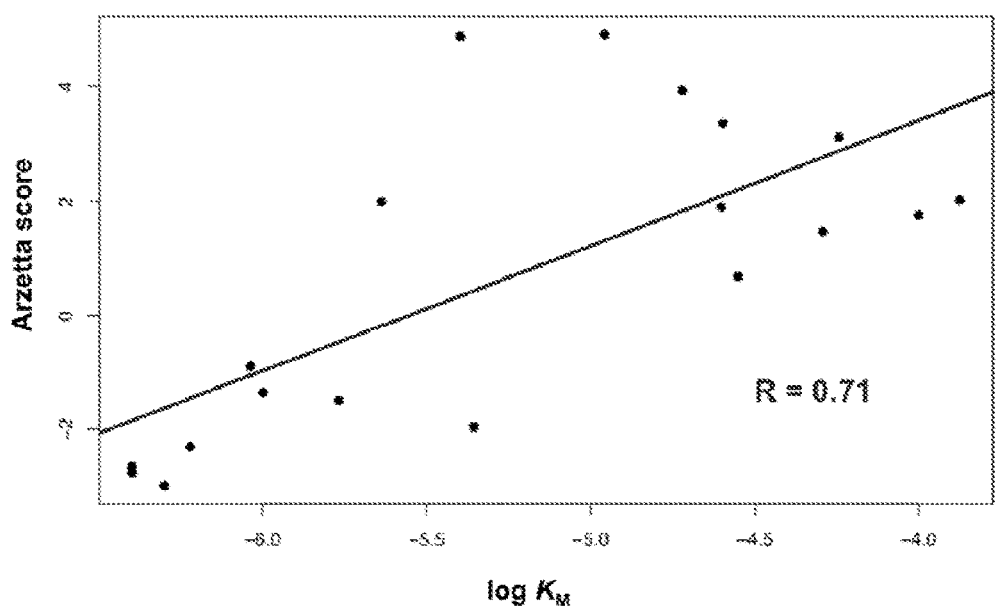
FIG. 19 is a correlation plot between the experimental substrate binding values ($\log_e(KM)$, x-axis) and the value of the Rosetta scoring function (y-axis) for the lowest score obtained after constrained docking of the transition structures, for each of the 19 beta-lactamase structures described in Example 2. The red-line is the least-square fit corresponding to the reported correlation coefficient R of 0.71

An ensemble of transition state structural models (transition structures) was first constructed in the program SPARTAN based on chemical analogs of the transition state for the reaction, and an ensemble of conformers were generated using a dedicated software derived from the software package and library OpenBabel, as described elsewhere herein. The resulting ensemble of structures is depicted in FIG. 18. Constraints between the four catalytic residues making up the functional site of the class A and C beta-lactamase considered (a SERINE-LYSINE-GLUTAMATE or SERINE-LYSINE-ASPARTATE triad, and an additional residue contributing its backbone amide to the oxyanion hole in addition to the catalytic serine's) and the transition state structures were defined and encoded in several constraint files (see FIG. 14 to FIG. 17). Different constraint files for class A for both the (R)- and (S)-benzyl-penicillin and class C for both the (R)- and (S)-benzyl-penicillin were specified. The ensemble of the transition structures were computationally docked in each of the 19 experimentally derived crystal structure, under the constraints defined for the functional site and the score of the best scoring transition structures in each of the 19 structures were compared to the logarithm of the $K_M$ for the substrate benzyl-penicillin that was measured experimentally. The result, which can be found in FIG. 19, shows that the computed score correlates extremely well (R=0.71) with the experimentally measures of $K_M$ demonstrating that the invention allows the automated selection ("identification") of sequences among a database of structures of the enzymes that will catalyze the hydrolysis of the antibiotic benzyl-penicillin.

Example 3

Figure 20:
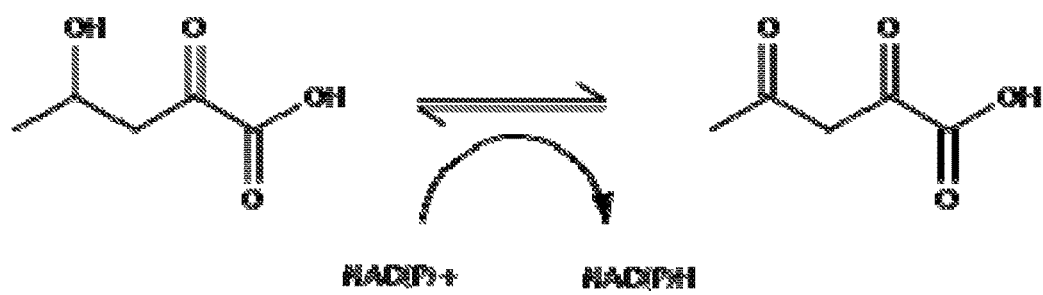
FIG. 20 depicts the NAD(P)+ dependent oxidation of 4-hydroxy-2-oxo-pentanoic acid into 2,4-dioxo-pentanoic acid. Because the in the reduced form the substrate has a stereo center at position 4, the substrate can have two stereoisomer, 4(R)-hydroxy-2-oxo-pentanoic acid and 4(S)-hydroxy-2-oxo-pentanoic acid.

Computational Identification of NAD(P)H Dependent Dehydrogenase Oxidizing 4-Hydroxy-2-Oxo-Pentanoic Acid into 2,4-Dioxo-Pentanoic Acid In this example, the aim is to computationally identify sequences from a structural database that catalyze yet another reaction: the oxidation of 4-hydroxy-2-oxo-pentanoic acid into 2,4-dioxo-pentanoic acid (reaction depicted in FIG. 20). Contrary to Examples 1 and 2, which represent benchmarks aimed at validated the ability of the disclosed method to predict the experimentally measured, relative catalytic efficiency of a set of related enzymes for which a crystal structure was available, this example demonstrates the use of the invention to computationally identify a particular catalytic activity (the oxidation of 4-hydroxy-2-oxo-pentanoic acid into 2,4-dioxo-pentanoic acid) among a diverse set of protein sequences known to catalyze similar and related reactions but whose activity on the substrate of interest (4-hydroxy-2-oxo-pentanoic acid) is not known.

Dehydrogenase enzymes catalyze the reversible oxidation of alcohols to the corresponding aldehydes, ketones or carboxylic acid (when first characterized in the oxidation direction, they are sometimes named carbonyl reductases). The largest class of dehydrogenase enzymes employ a nicotinamide redox cofactor such as NAD/NADH or NADP+/NADPH, collectively referred to as NAD(P)H-dependent dehydrogenases. A great variety of NAD(P)H-dependent dehydrogenases have been found and characterized and they are grouped, under the Enzyme Classification commission, in the subclass EC 1.1.1.* where the * represents a number between 1 and 363 (according to the BRENDA database (Schomburg et al., BRENDA, the enzyme database: updates and major new developments, Nucleic Acid Research 32(1):431-433 (2004)) as of March 2014). Our target reaction can theoretically be catalyzed by a NAD(P)H-dependent dehydrogenase enzyme. Therefore, we started by constructing a database of dehydrogenase sequences that would be representative of the enzymes contained in the EC subclass 1.1.1.* while having been biochemically characterized and for which at least one crystal structure existed. For each of the 363 entries in the BRENDA database numbered from 1.1.1.1 to 1.1.1.363, the database record were inspected for the availability of a crystal structure at a resolution better than 2.8 Å. When no crystal structure entry existed in the BRENDA database, a manual search by EC number (for example, 1.1.1.15) was done in the structural PDB database. If no hit was obtained in the PDB, the entry was not considered further. If at least one high-resolution crystal structure was found, the associated literature was carefully reviewed and all the structures found for this particular entry reviewed manually for the presence of the enzyme cofactor NAD+/NADH or NADP+/NAD(P)H or chemical analogs such as nicotinamide-8-iodo-adenine-dinucleotide (PDB code 8ID). If no cofactor or chemical analog was present, a structural homology search was performed to find similar crystal structures with an enzyme cofactor or chemical analog present and in such case this information used to manually place the cofactor/chemical analog in the query structure. In cases where only a chemical analog of the cofactor was available, it was manually replaced with a model of the actual cofactor. This was achieved through atom-atom superposition between the chemical analog 3D structure present in the crystal structure and a template model of NAD+ or NADP+, depending on the enzyme entry cofactor dependence. When NADH or NADPH was present in the crystal structure, it was replaced by NAD+ or NADP+, respectively.

This led to a database with a total of 98 sequence/structure entries. FIG. 27 contains a table listing the entries in this database. Each sequence (and structure thereof) is associated to one EC number in the form 1.1.1.x except for the EC class EC 1.1.1.1, 1.1.1.2, 1.1.1.35, 1.1.1.95 and 1.1.1.184 where respectively 3, 3, 2, 2 and 2 different sequences and structures representatives were kept, due to either the size of that subclass or different cofactor specificities. For each entry in the database, a detailed literature search was carried out to determine the catalytic mechanism and the active site residues. When no clear mechanisms or catalytic residues are known, each structure is visually inspected. Mechanisms were classified into subclasses based on preexisting classification found in the literature and the different constellation of catalytic residues observed. For instance, three large subclasses in our database correspond to archetype active site configurations from dehydrogenases subclasses Short Chain Dehydrogeneases/Reductases (SDR) as described in Persson et al., *A super-family of medium-chain dehydrogenases/reductases (MDR), Eur. J. Biochem.,* 226:15-22 (1994), Medium Chain Dehydrogenases/Reductases (MDR) as described in Oppermann et al., *Short-chain dehydrogenases/reductases (SDR) the* 2002 *update, Chemico-biological interactions,* 143-144:247-253 (2003) and the Aldo-Keto reductases (AKR) as reviewed in Sanli et al., *Structural Biology of the Aldo-Keto Reductase family of enzymes, Cell Biochemistry and Biophysics,* 38:79-101 (2003).

Figure 22:
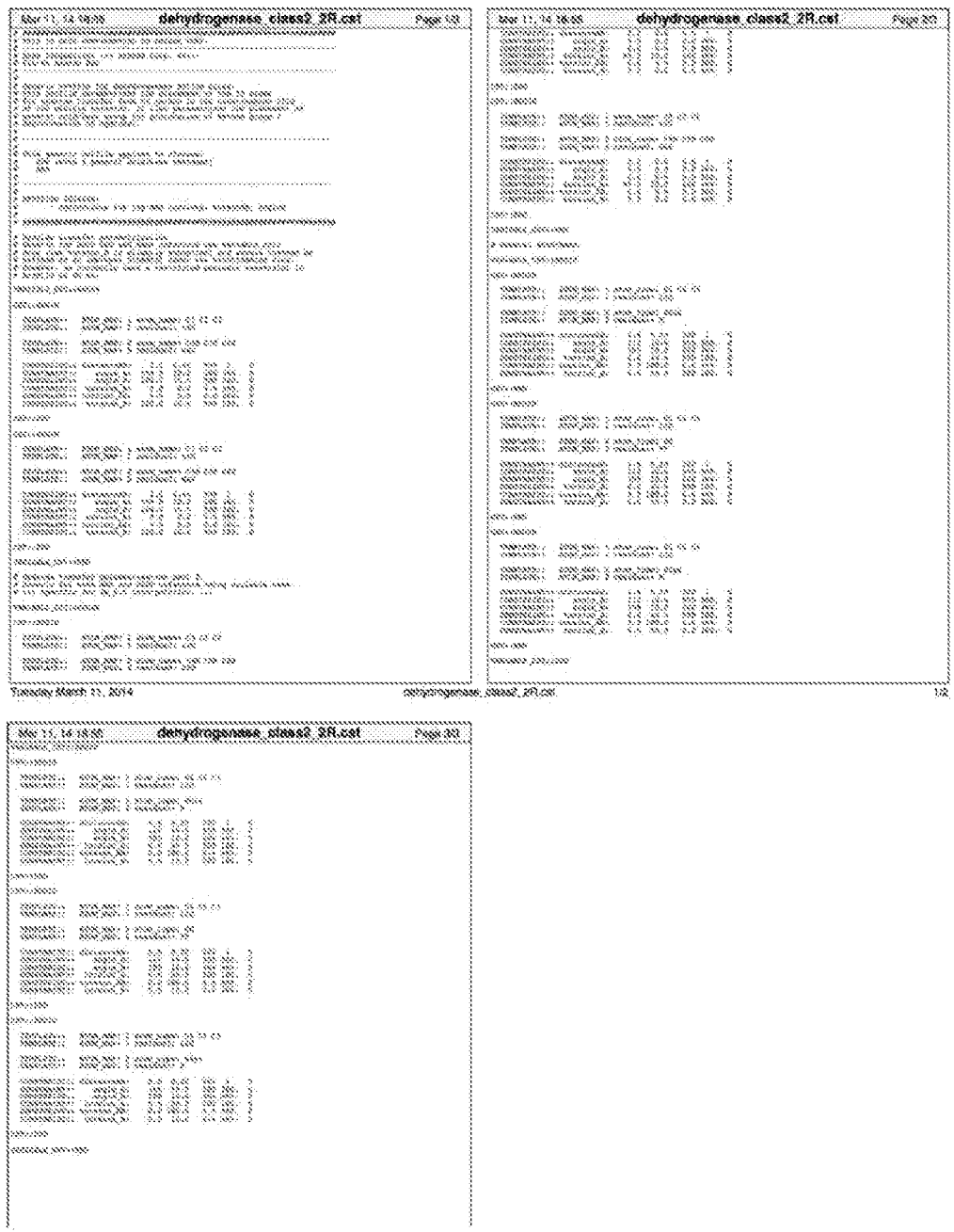
FIG. 22 is a copy of the parameterization file (cstfile) used to model the active site of a dehydrogenase for the oxidation of 4(R)-hydroxy-2-oxo-pentanoic acid into 2,4-dioxo-pentanoic acid and perform constrained-docking into a database of 87 dehydrogenase structures. The five different blocks of statements delimited by the CST::BEGIN and CST::END statements correspond to each of the catalytic residues 1, 2, 3 and 4 in FIG. 13. Note that because the catalytic residue 1 (Serine) is involved in two different ways in the active site (as the nucleophile and as provided one key backbone hydrogen bond to form the oxyanion hole), it is attached to two blocks instead of one.
Figure 23:
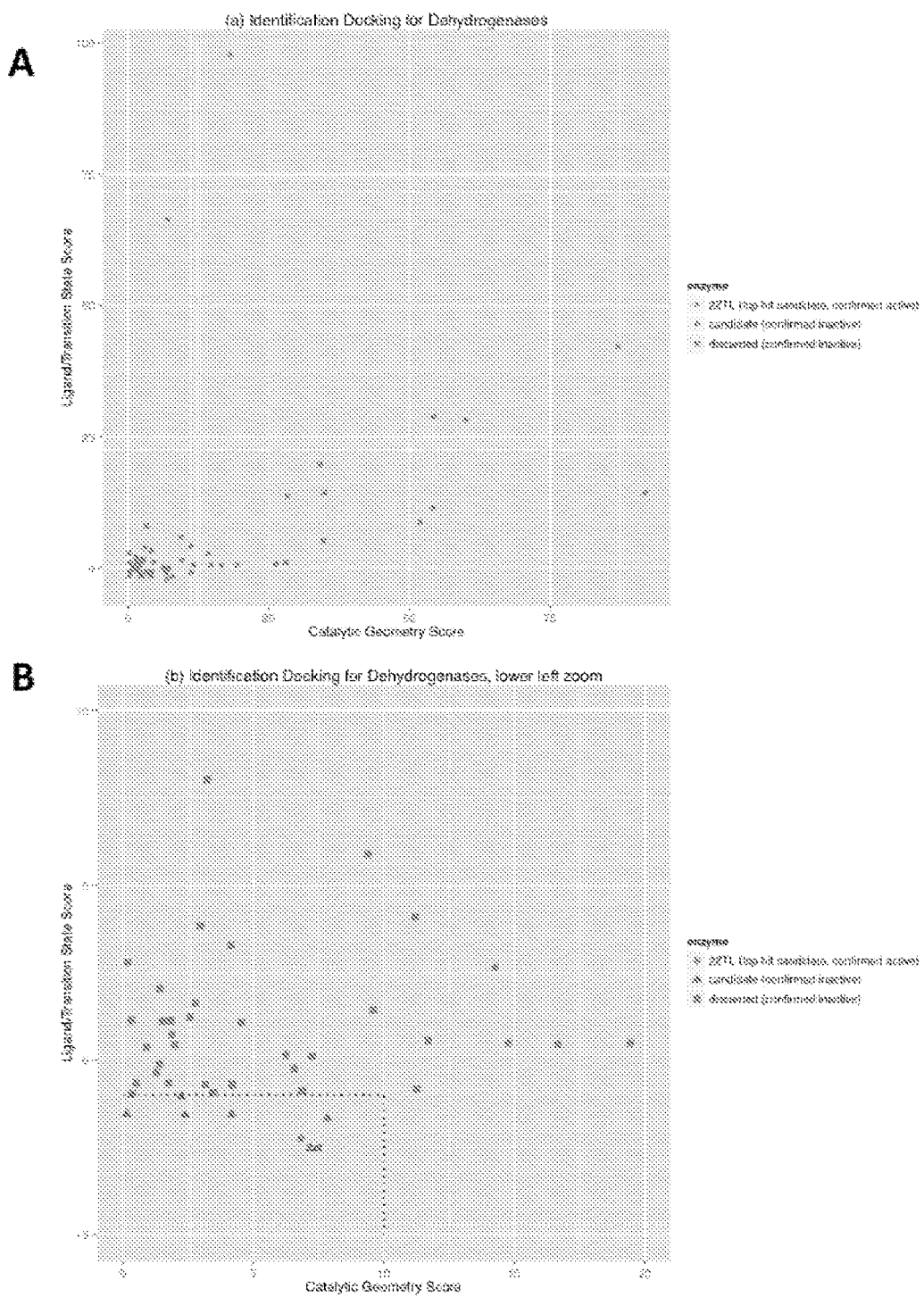
FIG. 23 represents an embodiment of the invention used to computationally predict the activity of a set of dehydrogenases towards a substrate of interest. The docking of the transition state model was run over 87 non-MDR dehydrogenases to determine candidates to catalyze the oxidation of 4-hydroxy-2-oxo-pentanoic acid into 2,4-dioxo-pentanoic. During the docking run, 30 of the enzymes failed coarse quality filters and were discarded, and are not shown on these plots. For the remaining 57 enzymes, the docking model exhibiting the best catalytic geometry is shown. Panel A shows the results for the remaining set of 57 enzymes, while panel B is zoomed into the lower left hand corner to show the selected candidates. The six candidates selected by the quality metrics are shown within the box whose boundaries are delineated by the dotted lines, indicating the catalytic geometry score cutoff of 10.0 and the ligand (transition state) score cutoff of −1.0. The top hit was expected to be 3-hydroxybutyrate dehydrogenase from *Pseudomonas fragi* (EC number EC1.1.1.30 and PDB code 2ZTL), having the best ligand score of −2.23 Rosetta Energy Units, which was confirmed by experimental testing of the entire set of dehydrogenases, where 2ZTL was found to be the only enzyme catalyzing the desired reaction, with a kcat/Km of 47.59 $M^{-1} s^{-1}$.

For each subclass, an active site model for the reaction of interest, the oxidation of 4-hydroxy-2-oxo-pentanoic acid into 2,4-dioxo-pentanoic acid is constructed. The active site is composed of a substrate/transition state/product model, the definition of catalytic residues and a set of geometrical constraints encoded in a cstfile, as in the case of Examples 1 and Examples 2. In this case, the substrate/transition state/product was built as a consensus model that linearly interpolates between the substrate (reduced hydroxyl at position 4 in 4-hydroxy-2-oxo-pentanoic acid) and the product of the oxidation reaction (oxidized ketone at position 4 in 2,4-dioxo-pentanoic acid). The geometry of the resulting model can be seen in FIG. 21. Catalytic residues common to the 98 dehydogenases in the database were identified (including different possible variants) and corresponding geometrical constraints were defined based on literature values available in the literature. This led to active sites constraints as depicted in the listed of FIG. 22.

Figure 24:
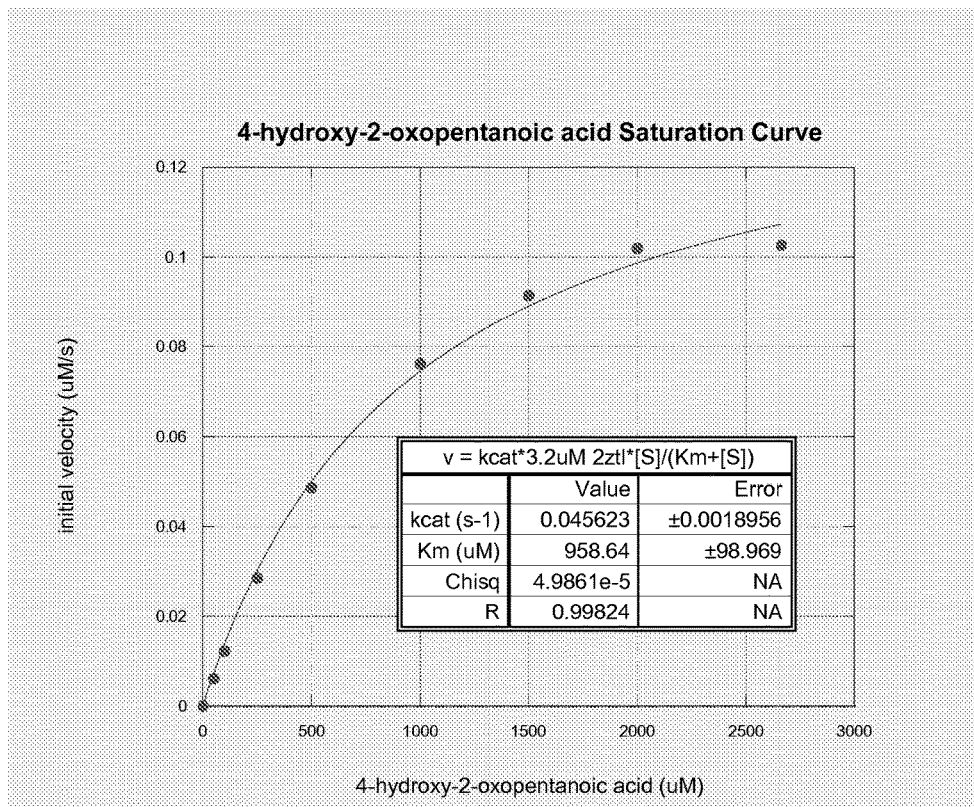
FIG. 24 shows the Michaelis-Menten kinetics of the enzyme 2ZTL for the oxidation of 4-hydroxy-2-oxo-pentanoic acid into 2,4-dioxo-pentanoic acid. The absorbance at 340 nm was monitored every 8 s on a spectrophotometer. An increase in absorbance corresponds to the formation of NADH or NADPH coupled to the oxidation of the substrate. The initial concentration of the substrate 4-hydroxy-2-oxo-pentanoic acid was set 3.3 mM and that of NAD+ or NADP+ at 1 mM. The substrate was obtained as the lactonized form from a third-party chemical synthesis company and was lactonized by incubating it in the enzyme assay buffer with the Ca-dependent enzyme paraxonase 3 (PON3) for 30 min at room temperature. An initial lactone concentration of 10 mM was used which yielded a final equilibrium concentration of 3.3 mM linear substrate and 6.7 mM lactone at pH 7.0. Assay buffer was 50 mM HEPES/lmM CaC12 pH 7.0. The enzyme concentration was 3.504. The curve was fitted using a Michaelis-Menten model and yielded a kcat/Km of 47.59 $M^{-1} s^{-1}$.

Similar to what is demonstrated in Example 1 and Example 2, computational predictions were made as to which of the 87 non-MDR dehydrogenase sequences in the database would demonstrate enzymatic activity. Following the method described elsewhere herein, docking of the ensemble of transition state models was run over the 87 non-MDR dehydrogenase structures under the constraints defined in the active site. During the docking run, 30 of the enzymes failed coarse quality filters and were discarded, and are not shown on these plots. For the remaining 57 enzymes, the docking model exhibiting the best catalytic geometry was selected. Selecting those models that have a catalytic geometry score cutoff of 10.0 and the ligand (transition state) score cutoff of −1.0 predicts 6 candidates that should activity towards the reaction of interest. The genes coding for all 87 sequences in the database (including the ones that are predicted to be very unfavorable for transition state binding and therefore unlikely to catalyze the reaction) were synthetized, cloned into variants of pET29 vectors with a 6-HIS tag, transformed into *E coli* BL21 strains, overexpressed and purified by Nickel affinity chromatography. Enzymatic activity was assayed by measuring the absorbance at 340 nm every 8 s on a spectrophotometer. Increase in absorbance corresponds to the formation of NADH or NADPH. The initial concentration of the substrate 4-hydroxy-2-oxo-pentanoic acid was set at 3.3 mM and that of NAD+ or NADP+ at 1 mM. Buffer was 50 mM HEPES/1 mM CaC12 pH 7.0. Enzyme concentration depended on expression level and was not normalized. Out of the 6 sequences selected by the computational identification method, the lowest scoring hit (−2.23 Rosetta Energy Units, therefore the sequence predicted to have the highest catalytic activity) was 3-hydroxybutyrate dehydrogenase from *Pseudomonas fragi* (EC number EC1.1.1.30 and PDB code 2ZTL) This is indeed confirmed by experimental assay where 2ZTL was found to catalyze the oxidation of 4-hydroxy-2-oxo-pentanoic acid with a kcat/Km of 47.59 $M^{-1} s^{-1}$ (see FIG. 24). All the remaining 86 sequences, including the 6 other sequences that would be selected using our cutoffs, were found to have no activity towards the desired reaction.

Figure 25:
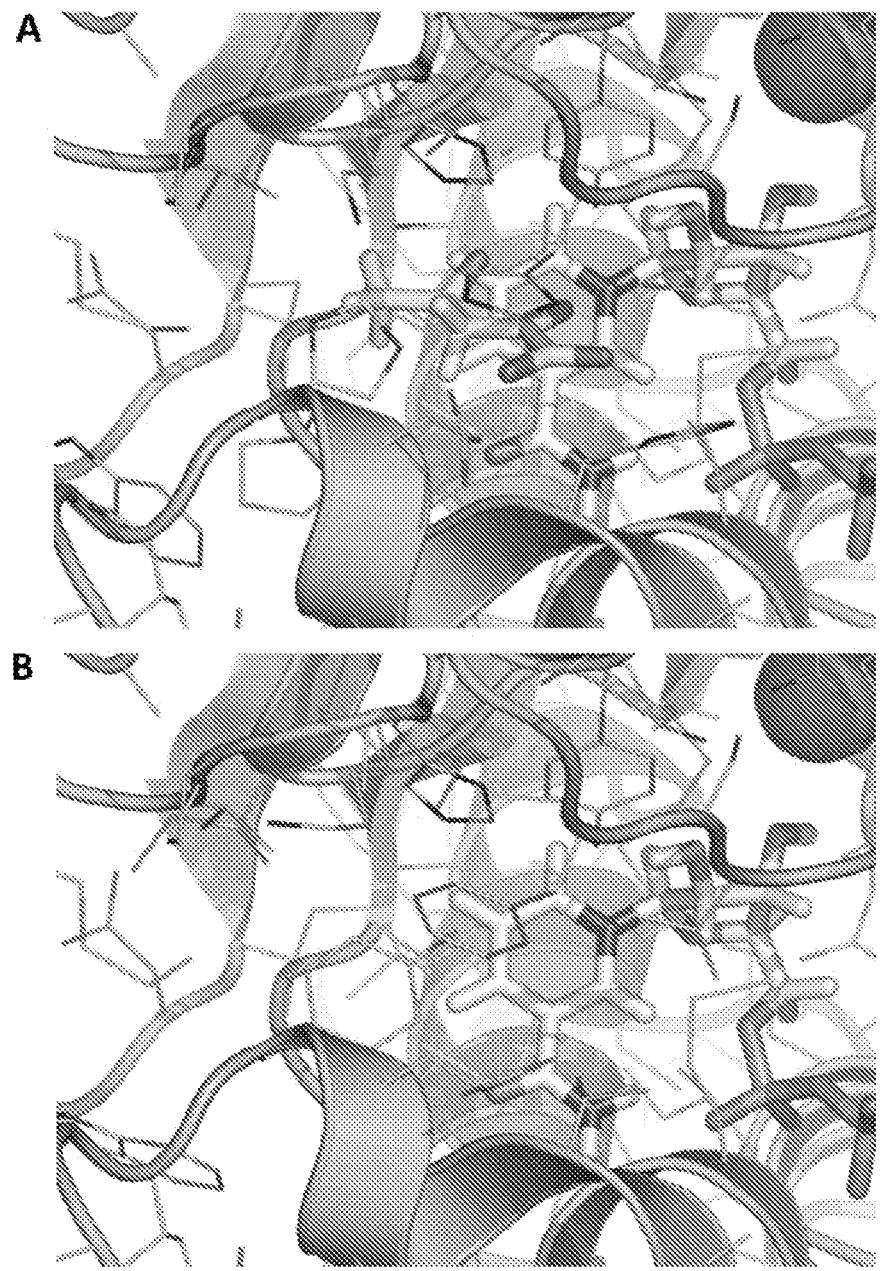
FIG. 25 depicts the use of the invention to rapidly design novel dehydrogenases able to oxidize 4-hydroxy-2oxo-pentanoic acid into 2,4-dioxo-pentanoic acid as described in Example 4. Panel A shows the geometry and identity of the active site residues for the wild-type dehydrogenase trihydroxynaphthalene reductase from *Magnaporthe grisea* as can be observed in the crystal structure deposited in the PDB structural database under the PDB code 1DOH (the structural template). Panel B shows the geometry and residue identities in the redesigned active site. The protein mainchain is represented in cartoons, the protein residues with lines. The position of the residues that are redesigned is in salmon color, the position of the residues that are left unchanged in cyan. The NADPH cofactor is represented in sticks and its nitrogen atoms are in blue, oxygen atoms in red and carbon atoms in light grey. The transition state model is represented in sticks and its nitrogen atoms are in blue, oxygen atoms in red, and carbon atoms in yellow.
Figure 26:
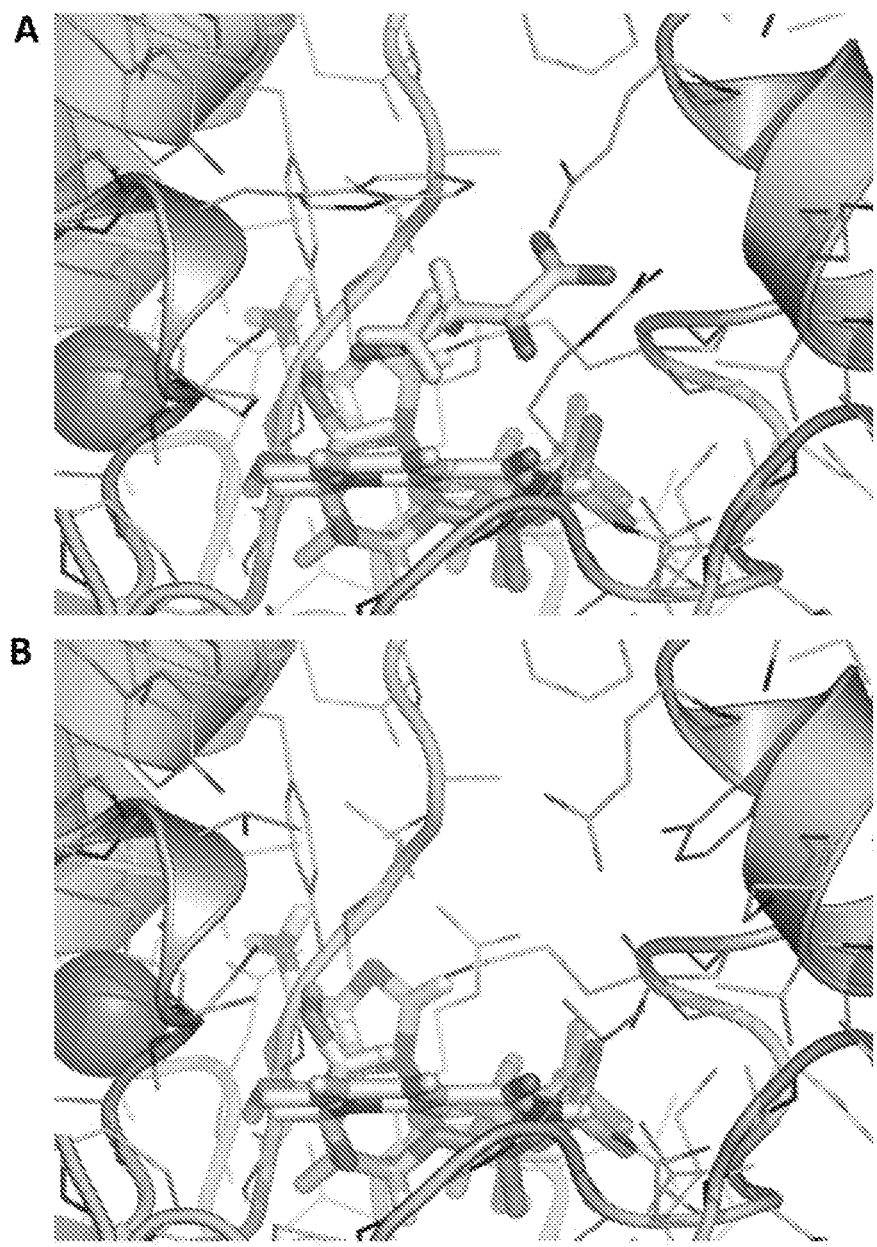
FIG. 26 depicts the use of the invention to rapidly design novel dehydrogenases able to oxidize 4-hydroxy-2oxo-pentanoic acid into 2,4-dioxo-pentanoic acid as described in Example 4. Panel A shows the geometry and identity of the active site residues for the wild-type dehydrogenase salutaridine reductase from *Papaver somniferum* as can be observed in the crystal structure deposited in the PDB structural database under the PDB code 3026 (the structural template). Panel B shows the geometry and residue identities in the redesigned active site. The protein mainchain is represented in cartoons, the protein residues with lines. The position of the residues that are redesigned is in salmon color, the position of the residues that are left unchanged in cyan. The NADPH cofactor is represented in sticks and its nitrogen atoms are in blue, oxygen atoms in red and carbon atoms in light grey. The transition state model is represented in sticks and its nitrogen atoms are in blue, oxygen atoms in red, and carbon atoms in yellow.

A transition state model was iteratively docked in the active site of each structural entry of the 87 non-MDR dehydrogenase database under the geometrical constraints defined in the active model described supra and elsewhere herein, and the active site pocket redesigned after each docking attempt. A total of 3 cycles of docking and design were used (each cycles being comprised of several hundreds attempts in a metropolis Monte Carlo scheme, as described for example in Richter et al., *de novo enzyme design using ROSETTA*3, *PloS ONE* 6(5): e19230 (2011)). Designs were selected using the ligand, here transition state model, score computed in Rosetta Energy Unit. A ligand score lower than −2.0 was considered acceptable to be selected for further filtering. This resulted in 144 novel sequences. Those sequences passing the ligand score cutoff were further screened using a combination of metrics, including shape-complementarity, chemical complementarity and the number of unsatisfied hydrogen bonding donors and acceptors in the transition state model and protein residues having between 2 to 14 mutations over the WT sequence of the template (that is, the original sequence listed in the 87 non-MDR dehydrogenase database). Two examples of designed sequences obtained with this mode of use of the invention, and the comparison to the WT sequence and active site and substrate binding pocket geometry are presented in FIG. 25 and FIG. 26. In FIG. 25, trihydroxynaphthalene reductase from *Magnaporthe grisea* (EC 1.1.1.252) is computationally redesigned to be converted into a 4-hydroxy-2oxo-pentanoic acid 4 oxidase. In FIG. 26, salutaridine reductase from *Papaver somniferum* (EC 1.1.1.248) is computationally redesigned to be converted into a 4-hydroxy-2oxo-pentanoic acid 4 oxidase. The genes encoding for the selected sequences are further synthetized, cloned into a variant of pET29 vector with a 6-HIS tag, transformed into *E coli* BL21*, expression strains, overexpressed and purified by Nickel affinity chromatography. Enzymatic activity is detected using the same protocol as described supra and elsewhere herein.

In a preferred embodiment, the methods contemplated herein was able to identify within a set of 87 natural enzymes catalyzing analogous reactions, one enzyme having the desired catalytic activity. Said activity has not been reported in a literature. Although for the purpose of validating the methodology all 87 members of the database were assayed, assaying the top 6 sequences selected by the computational methodology would have been sufficient to find the enzymatic activity of interest. Furthermore, to increase the number of hits for the reaction of interest, the iterative docking/design methodology disclosed herein was able to generate a library of designed sequence that has the desired activity. In particular embodiments, the methods contemplated herein are fully automated once the initial database of natural enzymes has been constructed. The database has been constructed by systematically reviewing all the enzymes of a given Enzyme Classification (EC) subclass represented by the first 3 numbers in the EC classification scheme and selecting representative members for which at least one crystal structure at a sufficient resolution was available and for which a sufficiently accurate active model can be built. Such databases can be constructed as to cover the entire EC subclasses, therefore covering the entire space of known enzymatic activities, grouped by EC subclasses. Therefore, in particular embodiments, the methods contemplated herein can be practiced for any class or type of chemical reaction that is known to be catalyzed by natural enzymes, even if the particular combination of reaction and substrate is not known to be catalyzed in nature.

Example 4

Figure 2:
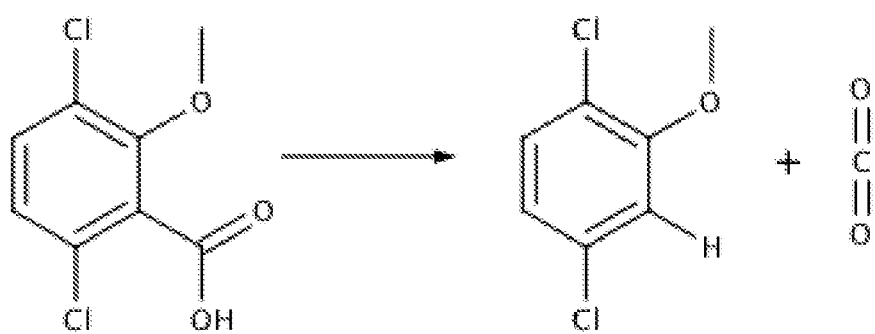
FIG. 2 shows the chemical reaction used in Example 3. This reaction is the decarboxylation of dicamba into 2,5-dichloroanisole.
Figure 3:
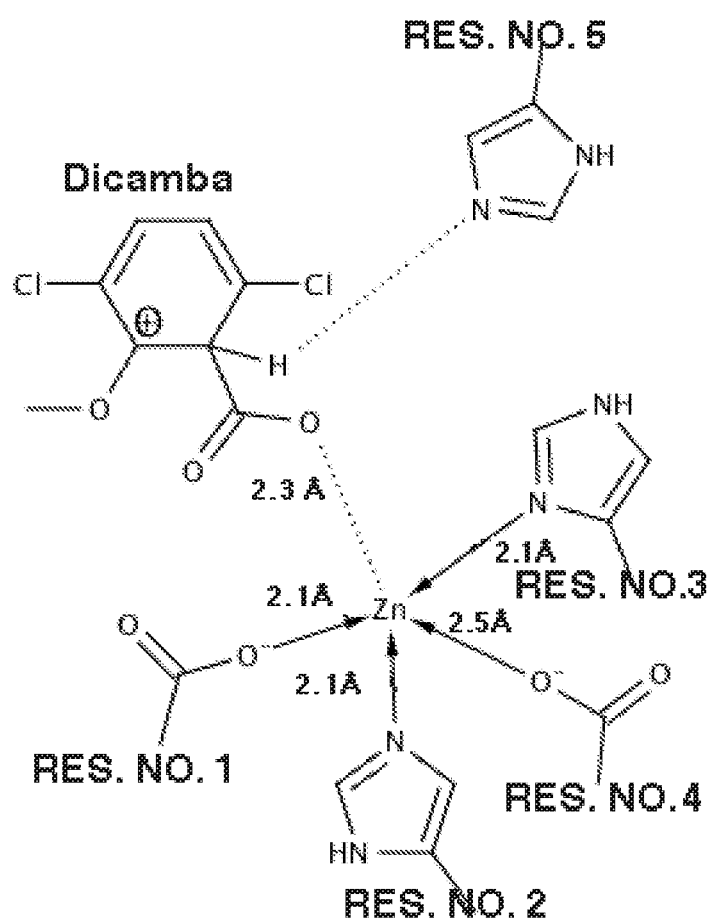
FIG. 3 shows the active site structure of decarboxylase enzymes used as templates to computationally identify a dicamba decarboxylase. The active site comprises 4 catalytic residues (RES NO 1 to RES NO 4) coordinating a metal ion (in the picture, a Zinc ion). In addition, a fifth catalytic residue, a Histidine (RES NO 5) acts as general acid/base and donates its proton to the decarboxylated ring.

Computational Identification and Experimental Validation of Novel Decarboxylase Enzymes Catalysing the Decarboxylation of Dicamba In this example, the aim is to computationally identify sequences catalyzing the decarboxylation of dicamba (see FIG. 2), a widely used herbicide. There are no records in the literature of an enzyme catalyzing the decarboxylation of dicamba. Discovering and/or designing novel sequences catalyzing this reaction is of paramount industrial importance as decarboxylation of dicamba inactivates its herbicidal activity, and such enzymes could serve for example for providing herbicide resistance to specific crops or to bioremediate soils contaminated with dicamba. The computational methods contemplated herein were used to identify novel decarboxylase enzymes catalysing the decarboxylation of dicamba.

An extensive literature review was carried out to determine the structural determinants of existing natural decarboxylase acting on aromatic carboxylated substrates such as benzoic acid. In particular, active sites of the type depicted in FIG. 3 were selected. These active sites comprise two key elements: a divalent ion, such as a zinc ion, is coordinated by several catalytic residues (usually Histidine and Aspartate/Glutamate residues) as well as by the carboxylate group of the substrate that will be decarboxylated. In addition, at least one additional general acid/base group (in FIG. 3, a Histidine) is used to donate a proton to the decarboxylated ring. Therefore, an active site parameterization (depicted in FIG. 5) was encoded based on the insights from this literature search: this parameterization is generic so that it can be used to model active sites where the metal coordination sphere is occupied by different residues from the protein side, such as Histidine, Aspartate/Glutamate and Cysteine.

An ensemble of transition state structural models (transition structures) was first constructed in the program SPARTAN for the decarboxylase reaction, and an ensemble of conformers were generated using a dedicated software derived from the software package and library OpenBabel, as described elsewhere herein. The resulting ensemble is depicted in FIG. 4. As can be seen in the picture, because dicamba is a small, relatively constrained ring, the ensemble of transition structures is relatively small.

Several initial sequences for which high-resolution crystal structures were available were used as seeds for a database search: all homologous sequences from the Protein Data Bank database were gathered (e value cutoff of 1.0) and each transition structure was docked in these structures, as described elsewhere herein, similar to Examples 1 and 2. The sequences corresponding to the lowest scoring structures were selected for further experimental characterization. In addition to docking the transition structures in the context of the natural (or WT) sequence, several rounds of transition structure docking and binding site redesign were carried out as described elsewhere herein.

In addition to searching for protein sequences for which an experimentally crystal structure is available, the NCBI nr (non-redundant) database of protein sequences was also searched for close homologs to the initial seed sequences of described above. One close homolog was selected for which no existing crystal structure is available (DC.12.001). A computational homology model homology model for DC12 was created as follows. Sequence database search of the DC12 amino acid sequence using JackHMMER and PSI-BLAST yielded 2GWG, a protein with sufficient homology for which a three-dimensional x-ray crystal structure existed in the protein databank. 2GWG has 58% amino acid sequence identity to DC12, but the crystal structure is not entirely complete in that there are two missing loops. According to the sequence and structural data, these two missing loops were predicted to be at or near the active site of DC12. In order to homology model DC12, we used the 2GWG backbone as the template structure. ROSETTA was used to thread the DC12 amino acid sequence onto the 2GWG backbone, sans the missing loop regions, and was subject to a round of optimization using sidechain repacking and minimization with full backbone flexibility and C-alpha harmonic constraints to tether together all C-alphas that are within 9 angstroms of each other. Top scoring models (sans the two loops) were selected by score quality metrics and manual inspection. Afterwards, ROSETTA was used to build the missing loops of DC12, one of length 9 residues and the other of length 15 residues, on top of these models using different approaches, including both fragment insertion+CCD, analytical loop closure, and structural refinement techniques. Top scoring homology models including the two loops were selected by score quality metrics and manual inspection, the transition structure of FIG. 4 iteratively docked into the resulting model and the identities of the remaining residues in the binding site selected by computational design, in order to design enzymatic activity for the decarboxylation of dicamba. As described below and shown in FIG. 6, the wild-type sequence DC.12.001 is not active, but one of the computational redesigned sequences based on the homology model and names DC.12.002 showed robust activity.

The DNA sequences corresponding to each of the protein sequences (both of the WT sequences and the redesigned sequences) were synthetized with the addition of a 6 HIS-tag and cloned into a suitable expression vector, expressed, purified and assayed for dicamba decarboxylase activity. The results for a set of 35 sequences can be found in FIG. 6. Out of the 35 sequences, 6 are natural (wild-type) sequences and 29 are designed sequences (i.e. each having at least 1 mutation over the wild-type sequence background). Out of the 35 sequences tested, 3 showed dicamba decarboxylase activity including one wild-type sequence (DC.4.001), one sequence redesigned from an existing, experimentally derived crystal structure template (DC.5.008) and one sequence redesigned from the homology model built (DC.12.002). This demonstrates that the disclosed invention enables the automated identification and design, from sequence databases, of novel enzymatic sequences catalyzing an industrially relevant chemical reaction.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for making a protein having an enzymatic activity, the method comprising:
   (a) obtaining a template structure of a template protein having the enzymatic activity, wherein the template protein is selected from the group consisting of: a carbonyl reductase, decarboxylase, and beta-lactamase;
   (b) preparing a functional site description based on the template structure, wherein the functional site description comprises (i) amino acid identities for each functional site amino acid residue, (ii) rotameric states for each functional residue, (iii) rotameric states for each ligand, and (iv) geometric placement of the functional residues with respect to said ligands;
   (c) computationally selecting one or more amino acid sequences having structural homology and/or sequence homology to the template protein having the enzymatic activity;
   (d) providing a structural model for each of the amino acid sequences selected in step (c);
   (e) selecting the amino acid sequences satisfying the functional site description comprising steps of computationally docking a ligand and optimizing positioning of amino acid side chains and main chain atoms of the amino acid sequences; and
   (f) recombinantly expressing and confirming the enzymatic activity for at least one of the amino acid sequences that satisfies the functional site description selected from step (e), thereby making the protein having the enzymatic activity.

2. The method of claim 1, wherein the template protein is a carbonyl reductase.

3. The method of claim 1, wherein the template protein is a decarboxylase.

4. The method of claim 1, wherein the template protein is a beta-lactamase.

5. The method of claim 1, wherein the functional site description is constructed using one or more of: quantum mechanical calculations, molecular mechanics, molecular dynamics, and human intuition, or combinations thereof.

6. The method of claim 1, wherein the template structure is a structure obtained by x-ray crystallography, nuclear magnetic resonance, or electron scattering or diffraction.

7. The method of claim 6, wherein the template structure includes a ligand(s), reaction substrate(s), reaction product(s) or transition state chemical analog in the functional site.

8. The method of claim 1, wherein the template protein has at least 85% sequence homology to the protein having the enzymatic activity.

9. The method of claim 1, wherein the amino acid sequences are selected by structural homology using one or more of structural alignment software selected from the group consisting of MAMMOTH/MAMMOTH-mult, CE/CE-MC, FATCAT/jFatCat, DALI/DaliLite, FAST, EXPRESSO, TopoFit, MUSTANG, GANGSTA/GANGSTA+, ProFit, and SABERTOOTH.

10. The method of claim 1, wherein the amino acid sequences are selected based on structural homology using protein domain databases selected from the group consisting of SCOP, DALI-database, Pfam, CATH, and TOPOFIT-DB.

11. The method of claim 1, wherein the amino acid sequences are selected by sequence homology using BLASTP, PSI-BLAST, DELTA-BLAST, HMMER, or JackHMMER.

12. The method of claim 1, wherein the structural model is constructed using ROSETTA, ROBETTA, TASSER, I-TASSER, HHpred, HHsearch, or MODELLER, or SWISS-MODEL.

13. The method of claim 1, wherein the structural model is created based on template structure.

14. The method of claim 13, wherein the structural model is created based on structural homologs of template structure.

15. The method of claim 1, wherein the ligand comprises one, two or all of the substrate(s), product(s) or transition state(s) related to the enzymatic activity.

16. The method of claim 1, wherein docking the ligand comprises positioning of the ligand in the functional site, with one or more of: protein side chain repacking, optimizing the position of the protein side-chain and main-chain atoms, and optimizing the ligand internal degrees of freedom by minimizing the energy of the ligand-structure interaction, the protein structure energy and/or the internal energy of ligand.

17. The method of claim 16, wherein the ligand comprises one, two or all of the substrate(s), product(s) or transition state(s) related to the enzymatic activity.

18. The method of claim 1, wherein optimizing positioning of amino acid sequences side chains and main chain atoms of the amino acid sequences comprises one or more of (i) minimizing the energy of the ligand and transition state-structure interaction; (ii) minimizing protein structure energy; and (iii) minimizing free energy of ligands and transition state.

19. The method of claim 1, wherein the amino acid sequences are selected after the structure models are optimized using fragment insertion, backbone perturbation, sidechain rotamer optimization, and minimization.

20. The method of claim 1, wherein the sequence identity is at least 40% amino acid sequence identity to the template protein having the enzymatic activity.

21. The method of claim 1, wherein the protein having an enzymatic activity is subjected to directed evolution and/or rational mutagenesis to improve said enzymatic activity.

22. The method of claim 1, where the iterations of step (e) are carried out until no new sequences are selected from the last iteration, or from the last 2 iterations.

* * * * *

UNITED STATES PATENT AND TRADEMARK OFFICE
CERTIFICATE OF CORRECTION

PATENT NO. : 10,025,900 B2
APPLICATION NO. : 14/776532
DATED : July 17, 2018
INVENTOR(S) : Zanghellini et al.

Page 1 of 1

It is certified that error appears in the above-identified patent and that said Letters Patent is hereby corrected as shown below:

On the Title Page

Item [71], replace "Alexandre Zanghellini, Seattle, WA (US); Yih-En Andrew Ban, Seattle, WA (US); Eric Anthony Althoff, Seattle, WA (US); Daniela Grabs, Seattle, WA (US); Mihai Luchian Azoitei, Chapel Hill, NC (US)" with --ARZEDA CORP., Seattle, WA (US)--.

In the Claims

At Claim 20, Column 32, Line 46, replace "40%" with --90%--.

Signed and Sealed this
Twenty-fifth Day of December, 2018

Andrei Iancu
*Director of the United States Patent and Trademark Office*